(12) United States Patent
Zhang

(10) Patent No.: US 12,188,069 B2
(45) Date of Patent: Jan. 7, 2025

(54) BIOCATALYST AND METHODS FOR SYNTHESIZING MIXED DISULFIDE CONJUGATES OF THIENOPYRIDINE COMPOUNDS

(71) Applicant: The Regents of the University of Michigan, Ann Arbor, MI (US)

(72) Inventor: Haoming Zhang, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 1146 days.

(21) Appl. No.: 16/966,359

(22) PCT Filed: Jan. 31, 2019

(86) PCT No.: PCT/US2019/016099
§ 371 (c)(1),
(2) Date: Jul. 30, 2020

(87) PCT Pub. No.: WO2019/152679
PCT Pub. Date: Aug. 8, 2019

(65) Prior Publication Data
US 2020/0370081 A1    Nov. 26, 2020

Related U.S. Application Data

(60) Provisional application No. 62/624,494, filed on Jan. 31, 2018.

(51) Int. Cl.
*C12P 17/16* (2006.01)
*A61K 31/4535* (2006.01)
*A61K 45/06* (2006.01)

(52) U.S. Cl.
CPC ........ *C12P 17/167* (2013.01); *A61K 31/4535* (2013.01); *A61K 45/06* (2013.01); *C12Y 106/02004* (2013.01)

(58) Field of Classification Search
CPC .............................................. C12Y 106/02004
See application file for complete search history.

(56) References Cited

U.S. PATENT DOCUMENTS

| | | | |
|---|---|---|---|
| 3,989,816 | A | 11/1976 | Rajadhyaksha |
| 4,444,762 | A | 4/1984 | Rajadhyaksha |
| 6,610,708 | B1 | 8/2003 | Asai et al. |
| 9,718,778 | B2 | 8/2017 | Zhang et al. |
| 2011/0236940 | A1 | 9/2011 | Yun et al. |
| 2012/0202256 | A1 | 8/2012 | Yun et al. |
| 2012/0329763 | A1 | 12/2012 | Kumar et al. |
| 2014/0242647 | A1 | 8/2014 | Coelho et al. |
| 2015/0093793 | A1 | 4/2015 | Yun et al. |
| 2016/0032330 | A1 | 2/2016 | Renata et al. |
| 2017/0073720 | A1 | 3/2017 | Yun et al. |
| 2017/0121341 | A1 | 5/2017 | Sun et al. |
| 2017/0159030 | A1 | 6/2017 | Jung et al. |
| 2020/0370081 | A1 | 11/2020 | Zhang |

FOREIGN PATENT DOCUMENTS

| | | |
|---|---|---|
| CN | 104105794 | 10/2014 |
| CN | 107177541 | 9/2017 |
| KR | 10-2011-0020525 | 3/2011 |
| KR | 2017 0029272 | 3/2017 |
| WO | 2005/017116 | 2/2005 |
| WO | 2009/047498 | 4/2009 |
| WO | 2013/076258 | 5/2013 |
| WO | 2014/058744 | 4/2014 |
| WO | 2014/109987 | 7/2014 |
| WO | 2015/040197 | 3/2015 |
| WO | 2016/038095 | 3/2016 |
| WO | 2016/176644 | 11/2016 |
| WO | 2019/040335 | 2/2019 |

OTHER PUBLICATIONS

Liu Y. et al Resonance Raman studies of Bacillus megaterium cytochrome P450 BM3 and biotechnologically important mutants. Journal of Raman Spectroscopy, Nov. 10, 2017, vol. 49, No. 2, pp. 287-297.
Feenstra, K. Anton, et al. Combining substrate dynamics, binding statistics, and energy barriers to rationalize regioselective hydroxylation of octane and lauric acid by CYP102A1 and mutants, Protein Sci. Mar. 2007;16(3):420-31.
Zhang, H. et al. The full-length cytochrome P450 enzyme CYP102A1 dimerizes at its reductase domains and has flexible heme domains for efficient catalysis, J Biol Chem. May 18, 2018;293(20):7727-7736.
Altschul. A protein alignment scoring system sensitive at all evolutionary distances. J Mol Evol. Mar. 1993;36(3):290-300.
Altschul et al., Basic local alignment search tool. J Mol Biol. Oct. 5, 1990;215(3):403-10.
Butler et al., Key mutations alter the cytochrome P450 BM3 conformational landscape and remove inherent substrate bias. J Biol Chem. Aug. 30, 2013;288(35):25387-25399.
Carmichael et al., Protein engineering of Bacillus megaterium CYP102. The oxidation of polycyclic aromatic hydrocarbons. Eur J Biochem. May 2001;268(10):3117-25.
Cryle et al., Are branched chain fatty acids the natural substrates for P450(BM3)? Chem Commun (Camb). Jun. 14, 2006;(22):2353-5.
Damsten et al., Application of drug metabolising mutants of cytochrome P450 BM3 (CYP102A1) as biocatalysts for the generation of reactive metabolites. Chem Biol Interact. Jan. 10, 2008;171(1):96-107.
Devereux et al., A comprehensive set of sequence analysis programs for the VAX. Nucleic Acids Res. Jan. 11, 1984;12(1 Pt 1):387-95.
Jeandet et al., Engineering microbial cells for the biosynthesis of natural compounds of pharmaceutical significance. Biomed Res Int. 2013;2013:780145. 13 pages.

(Continued)

*Primary Examiner* — Suzanne M Noakes
(74) *Attorney, Agent, or Firm* — Casimir Jones, S.C.; Robert A. Goetz

(57) ABSTRACT

The present invention relates to methods for synthesizing mixed disulfide conjugates of thienopyridine compounds with a genetically engineered variant of cytochrome P450 BM3 or CYP102A1 as a catalyst, and belongs to the field of chemical synthesis.

18 Claims, 7 Drawing Sheets
Specification includes a Sequence Listing.

(56) References Cited

OTHER PUBLICATIONS

Li et al., The structure of the cytochrome p450BM-3 haem domain complexed with the fatty acid substrate, palmitoleic acid. Nat Struct Biol. Feb. 1997;4(2):140-6.

Li et al., Directed evolution of the fatty-acid hydroxylase P450 BM-3 into an indole-hydroxylating catalyst. Chemistry. May 2, 2000;6(9):1531-6.

Miura et al., Omega-1, Omega-2 and Omega-3 hydroxylation of long-chain fatty acids, amides and alcohols by a soluble enzyme system from Bacillus megaterium. Biochim Biophys Acta. Jun. 23, 1975;388(3):305-17.

Ravichandran et al., Crystal structure of hemoprotein domain of P450BM-3, a prototype for microsomal P450's. Science. Aug. 6, 1993;261(5122):731-6.

Sawayama et al., A panel of cytochrome P450 BM3 variants to produce drug metabolites and diversify lead compounds. Chemistry. Nov. 2, 2009;15(43):11723-9.

Shaw et al., Synthesis of Biologically Active Piperidine Metabolites of Clopidogrel: Determination of Structure and Analyte Development. J Org Chem. Jul. 17, 2015;80(14):7019-32.

Silvain et al., Rapid P2Y12 inhibition: still an unmet medical need. Circ Cardiovasc Interv. Jun. 2012;5(3):328-31.

Zhang et al., CYP-independent inhibition of platelet aggregation in rabbits by a mixed disulfide conjugate of clopidogrel. Thromb Haemost. Dec. 2014;112(6):1304-11.

Zhang et al., Potent mechanism-based inactivation of cytochrome P450 2B4 by 9-ethynylphenanthrene: implications for allosteric modulation of cytochrome P450 catalysis. Biochemistry. Jan. 15, 2013;52(2):355-64.

Zhang et al., Significant Improvement of Antithrombotic Responses to Clopidogrel by Use of a Novel Conjugate as Revealed in an Arterial Model of Thrombosis. J Pharmacol Exp Ther. Oct. 2016;359(1):11-7.

International Search Report, International Patent Application No. PCT/US2019/016099, mailed Jun. 20, 2019, 17 pages.

EP Search Report, EP Patent Application No. 19746615.4, mailed Oct. 5, 2021, 14 pages.

Butler et al. "Key Mutations After the Cytochrome P450 BM3 Conformational Landscape and Remove Inherent Substrate Bias" The Journal of Biological Chemistry, Jul. 3, 2013.

Zhang et al. "CYP-independent inhibition of platelet aggregation in rabbits by a mixed disulfide conjugate of clopidogrel" Thrombosis and Haemostatis, Sep. 18, 2014, vol. 112, No. 6, pp. 1304-1311.

Sawayama et al. "A Panel of Cytochrome P450 BM3 Variants to Produce Drug Metabolites and Diversify Lead Compounds" Chemistry, Nov. 2, 2009, vol. 15, No. 43, pp. 11723-11729.

Seifert A. et al. "Rational design of a minimal and highly enriched CYP102A1 mutant library with improved regio-stereo- and chemoselectivity" Chembiochem, vol. 10, No. 5, Mar. 23, 2009, pp. 853-861.

FIG. 4A

Wild Type cDNA of 1541 to 4690 of wild-type B.megaterium cytochrome P-450:NADPH-P-450 reductase gene (see,e.g., Accession J04832)

```
1501                                                   atgacaatta aagaaatgcc
1561 tcagccaaaa acgtttggag agcttaaaaa tttaccgtta ttaaacacag ataaaccggt
1621 tcaagctttg atgaaaattg cggatgaatt aggagaaatc tttaaattcg aggcgcctgg
1681 tcgtgtaacg cgctacttat caagtcagcg tctaattaaa gaagcatgcg atgaatcacg
1741 ctttgataaa aacttaagtc aagcgcttaa atttgtacgt gattttgcag gagacgggtt
1801 atttacaagc tggacgcatg aaaaaaattg gaaaaaagcg cataatatct tacttccaag
1861 cttcagtcag caggcaatga aaggctatca tgcgatgatg gtcgatatcg ccgtgcagct
1921 tgttcaaaag tgggagcgtc taaatgcaga tgagcatatt gaagtaccgg aagacatgac
1981 acgtttaacg cttgatacaa ttggtctttg cggctttaac tatcgcttta acagctttta
2041 ccgagatcag cctcatccat ttattacaag tatggtccgt gcactggatg aagcaatgaa
2101 caagctgcag cgagcaaatc cagacgaccc agcttatgat gaaaacaagc gccagtttca
2161 agaagatatc aaggtgatga acgacctagt agataaaatt attgcagatc gcaaagcaag
2221 cggtgaacaa agcgatgatt tattaacgca tatgctaaac ggaaaagatc cagaaacggg
2281 tgagccgctt gatgacgaga acattcgcta tcaaattatt acattcttaa ttgcgggaca
2341 cgaaacaaca agtggtcttt tatcatttgc gctgtatttc ttagtgaaaa atccacatgt
2401 attacaaaaa gcagcagaag aagcagcacg agttctagta gatcctgttc caagctacaa
2461 acaagtcaaa cagcttaaat atgtcggcat ggtcttaaac gaagcgctgc gcttatggcc
2521 aactgctcct gcgttttccc tatatgcaaa agaagatacg gtgcttggag gagaatatcc
2581 tttagaaaaa ggcgacgaac taatggttct gattcctcag cttcaccgtg ataaaacaat
2641 ttggggagac gatgtggaag agttccgtcc agagcgtttt gaaaatccaa gtgcgattcc
2701 gcagcatgcg tttaaaccgt ttggaaacgg tcagcgtgcg tgtatcggtc agcagttcgc
2761 tcttcatgaa gcaacgctgg tacttggtat gatgctaaaa cactttgact ttgaagatca
2821 tacaaactac gagctggata ttaaagaaac tttaacgtta aaacctgaag gctttgtggt
2881 aaaagcaaaa tcgaaaaaaa ttccgcttgg cggtattcct tcacctagca ctgaacagtc
2941 tgctaaaaaa gtacgcaaaa aggcagaaaa cgctcataat acgccgctgc ttgtgctata
3001 cggttcaaat atgggaacag ctgaaggaac ggcgcgtgat ttagcagata ttgcaatgag
3061 caaaggattt gcaccgcagg tcgcaacgct tgattcacac gccggaaatc ttccgcgcga
3121 aggagctgta ttaattgtaa cggcgtctta taacggtcat ccgcctgata acgcaaagca
3181 atttgtcgac tggttagacc aagcgtctgc tgatgaagta aaaggcgttc gctactccgt
3241 atttggatgc ggcgataaaa actgggctac tacgtatcaa aaagtgcctg cttttatcga
3301 tgaaacgctt gccgctaaag gggcagaaaa catcgctgac cgcggtgaag cagatgcaag
3361 cgacgacttt gaaggcacat atgaagaatg gcgtgaacat atgtggagtg acgtagcagc
3421 ctactttaac ctcgacattg aaaacagtga agataataaa tctactcttt cacttcaatt
3481 tgtcgacagc gccgcggata tgccgcttgc gaaaatgcac ggtgcgtttt caacgaacgt
3541 cgtagcaagc aaagaacttc aacagccagg cagtgcacga agcacgcgac atcttgaaat
3601 tgaacttcca aaagaagctt cttatcaaga aggagatcat ttaggtgtta ttcctcgcaa
3661 ctatgaagga atagtaaacc gtgtaacagc aaggttcggc ctagatgcat cacagcaaat
3721 ccgtctggaa gcagaagaag aaaaattagc tcatttgcca ctcgctaaaa cagtatccgt
3781 agaagagctt ctgcaatacg tggagcttca agatcctgtt acgcgcacgc agcttcgcgc
3841 aatggctgct aaaacggtct gcccgccgca taaagtagag cttgaagcct gcttgaaaa
3901 gcaagcctac aaagaacaag tgctggcaaa acgtttaaca atgcttgaac tgcttgaaaa
3961 atacccggcg tgtgaaatga aattcagcga atttatcgcc cttctgccaa gcatacgccc
4021 gcgctattac tcgatttctt catcacctcg tgtcgatgaa aaacaagcaa gcatcacggt
4081 cagcgttgtc tcaggagaag cgtggagcgg atatggagaa tataaaggaa ttgcgtcgaa
4141 ctatcttgcc gagctgcaag aaggagatac gattacgtgc tttatttcca ccacgcagtc
4201 agaatttacg ctgccaaaag accctgaaac gccgcttatc atggtcggac cgggaacagg
4261 cgtcgcgccg tttagaggct ttgtgcaggc gcgcaaacag ctaaaagaac aaggacagtc
4321 acttggagaa gcacatttat acttcggctg ccgttcacct catgaagact atctgtatca
4381 agaagagctt gaaaacgccc aaagcgaagg catcattacg cttcataccg cttttctcg
4441 catgccaaat cagccgaaaa catacgttca gcacgtaatg gaacaagacg gcaagaaatt
4501 gattgaactt cttgatcaag gagcgcactt ctatatttgc ggagacggaa gccaaatggc
4561 acctgccgtt gaagcaacgc ttatgaaaag ctatgctgac gttcaccaag tgagtgaagc
4621 agacgctcgc ttatggctgc agcagctaga agaaaaaggc cgatacgcaa aagacgtgtg
4681 ggctgggtaa
```

FIG. 4B – Wild type amino acid sequence for B.megaterium cytochrome P-450:NADPH-P-450 reductase gene (see,e.g., Accession J04832) (SED ID NO: 2)

```
tikempqpkt fgelknlpll ntdkpvqalm kiadelgeif kfeapgrvtr ylssqrlike      60
acdesrfdkn lsqalkfvrd fagdglftsw theknwkkah nillpsfsqq amkgyhammv     120
diavqlvqkw erlnadehie vpedmtrltl dtiglcgfny rfnsfyrdqp hpfitsmvra     180
ldeamnklqr anpddpayde nkrqfqedik vmndlvdkii adrkasgeqs ddllthmlng     240
kdpetgepld deniryqiit fliaghetts gllsfalyfl vknphvlqka aeeaarvlvd     300
pvpsykqvkq lkyvgmvlne alrlwptapa fslyakedtv lggeyplekg delmvlipql     360
hrdktiwgdd veefrperfe npsaipqhaf kpfgngqrac igqqfalhea tlvlgmmlkh     420
fdfedhtnye ldiketltlk pegfvvkaks kkiplggips psteqsakkv rkkaenahnt     480
pllvlygsnm gtaegtardl adiamskgfa pqvatldsha gnlpregavl ivtasynghp     540
pdnakqfvdw ldqasadevk gvrysvfgcg dknwattyqk vpafidetla akgaeniadr     600
geadasddfe gtyeewrehm wsdvaayfnl diensednks tlslqfvdsa admplakmhg     660
afstnvvask elqqpgsars trhleielpk easyqegdhl gviprnyegi vnrvtarfgl     720
dasqqirlea eeeklahlpl aktvsveell qyvelqdpvt rtqlramaak tvcpphkvel     780
eallekqayk eqvlakrltm lellekypac emkfsefial lpsirpryys isssprvdek     840
qasitvsvvs geawsgygey kgiasnylae lqegdtitcf istpqseftl pkdpetplim     900
vgpgtgvapf rgfvqarkql keqgqslgea hlyfgcrsph edylyqeele naqsegiitl     960
htafsrmpnq pktyvqhvme qdgkkliell dqgahfyicg dgsqmapave atlmksyadv    1020
hqvseadarl wlqqleekgr yakdvwag                                       1048
```

FIG. 4C
Optimized CDNA sequence of BM3 (The underlined section indicates hexaHistag)(SEQ ID NO: 3)

ATG<u>CACCATCATCATCATCAT</u>ATTAAGGAGATGCCGCAGCCAAAAACATTCGGCGAA

CTCAAAAACTTACCATTACTGAATACCGACAAACCGGTCCAAGCACTGATGAAAATT

GCGGACGAATTAGGTGAAATCTTCAAATTCGAGGCGCCCGGTCGCGTAACACGTTAT

TTATCCAGTCAGCGCCTTATCAAAGAAGCGTGTGATGAAAGTCGTTTTGATAAAAAT

CTGTCCCAGGCACTTAAATTTGTTCGTGACTTTTTCGGTGATGGCCTGTTTACCTCT

TGGACTCATGAAAAAACTGGAAAAAAGCGCATAATATCTTGCTTCCGTCGTTTTCG

CAGCAGGCAATGAAAGGTTACCATGCCATGATGGTCGATATTGCCGTCCAGCTGGTG

CAAAAATGGGAACGTCTTAACGCTGATGAACATATTGAAGTGCCCGAAGACATGACC

CGTCTGACGCTGGATACTATTGGACTGTGCGGGTTCAACTATCGTTTCAACTCCTTC

TACCGTGATCAGCCACATCCGTTTATTACTTCTATGGTCCGCGCCTTAGACGAAGCC

ATGAACAAACTGCAGCGCGCCAACCCAGACGACCCAGCTTATGATGAGAATAAACGT

CAGTTTCAAGAAGACATCAAAGTCATGAACGACTTAGTGGATAAAATTATTGCAGAC

CGTAAAGCGAGCGGCGAACAGAGTGATGACCTGCTTACCCACATGCTGAATGGTAAA

GATCCAGAGACCGGCGAGCCGTTAGATGATGAAAATATTCGCTACCAGATCATTACC

TTTTTAATCGCAGGACACGAAACAACAAGTGGACTGCTCAGCTTTGCACTCTACTTT

CTGGTTAAAAACCCGCATGTTCTGCAAAAAGCAGCGGAAGAGGCCGCCCGTGTGCTG

GTCGATCCGGTTCCCAGCTATAAACAGGTCAAACAGTTAAAATACGTGGGCATGGTC

TTAAACGAGGCTCTGCGCTTATGGCCAACAGCACCAGCATTTTCGTTATATGCAAAA

GAAGATACCGTTCTGGGAGGAGAATACCCGTTAGAAAAAGGCGACGAGCTTATGGTG

CTGATCCCACAGTTACACCGTGATAAAACCATTTGGGGCGACGATGTGGAAGAATTT

CGCCCAGAACGTTTCGAGAACCCTAGCGCAATTCCACAGCATGCCTTCAAACCCTTC

GGGAACGGTCAGCGCGCGTGCATTGGGCAGCAGTTCGCGCTGCATGAAGCAACTTTG

GTGTTAGGCATGATGCTGAAACACTTTGATTTTGAAGACCACACGAATTATGAACTG

GATATTAAAGAAACCCTGACACTGAAACCAGAAGGATTCGTAGTTAAAGCGAAAAGC

AAAAAGATTCCGCTGGGTGGCATTCCGAGCCCATCCACCGAACAGAGCGCGAAAAAA

GTTCGGAAAAAGGCGGAAAATGCGCACAATACCCCCTTGTTAGTCCTTTACGGCTCA

AATATGGGCACAGCAGAAGGCACCGCACGTGACTTAGCCGATATTGCAATGAGCAAG

GGTTTCGCGCCCCAAGTCGCGACCTTGGATTCACACGCTGGAAACCTGCCGCGGGAA

GGCGCCGTCCTTATCGTTACTGCCTCATATAACGGTCACCCTCCGGACAATGCGAAA

CAATTTGTGGACTGGTTAGATCAAGCCTCGGCCGACGAAGTGAAAGGCGTTCGTTAT

TCTGTTTTTGGATGTGGGGATAAAAACTGGGCGACGACGTACCAAAAAGTCCCTGCT

TTTATTGATGAAACGTTGGCTGCAAAAGGTGCAGAAAACATTGCAGACCGTGGCGAA

GCAGACGCGAGCGACGACTTTGAAGGTACCTATGAGGAATGGCGTGAACACATGTGG

AGTGATGTCGCCGCTTACTTCAACTTAGATATTGAAAATTCCGAAGATAATAAAGT

ACCCTGAGCTTGCAATTCGTGGACTCGGCTGCCGACATGCCGCTCGCTAAAATGCAC

GGGGCGTTTAGTACGAATGTAGTGGCTTCCAAAGAGTTGCAACAACCCGGTAGCGCA

CGCTCGACCCGGCACCTGGAAATTGAATTACCGAAGGAAGCGTCTTATCAGGAAGGA

FIG. 4C (cont'd)

```
GATCATCTGGGTGTAATCCCACGCAATTACGAAGGTATTGTTAATCGCGTTACCGCG
CGTTTTGGTTTAGATGCCTCCCAACAAATCCGTTTAGAAGCAGAAGAAGAAAAACTC
GCGCATTTACCCTTAGCCAAAACCGTTTCGGTCGAAGAACTGCTGCAATATGTTGAA
CTTCAGGACCCTGTGACCCGTACCCAGCTCCGTGCCATGGCCGCGAAAACAGTATGC
CCACCCCACAAAGTTGAATTAGAGGCGCTGTTAGAGAAACAAGCATACAAAGAACAA
GTGTTAGCTAAGCGTCTGACCATGTTAGAGTTACTGGAGAAATATCCGGCGTGCGAG
ATGAAATTCTCAGAATTCATTGCATTGTTGCCGAGCATTCGTCCGCGGTATTACAGT
ATCTCGAGCTCACCGCGCGTTGATGAAAAACAGGCCTCTATTACGGTCTCCGTAGTT
TCCGGCGAAGCCTGGAGCGGGTATGGAGAATATAAAGGAATTGCTAGCAACTATCTC
GCGGAGCTGCAAGAGGGCGACACTATTACATGCTTCATTTCTACGCCGCAATCCGAA
TTTACACTGCCGAAAGACCCGGAAACGCCACTCATTATGGTAGGCCCAGGTACTGGC
GTAGCGCCATTTCGCGGATTCGTTCAGGCTCGTAAACAGTTGAAAGAACAAGGTCAA
AGTCTTGGCGAAGCACATTTATACTTCGGCTGCCGCTCGCCGCATGAGGACTATCTC
TATCAGGAAGAATTGGAGAACGCACAGAGTGAGGGCATTATCACCTTGCATACGGCT
TTTTCTCGCATGCCTAATCAACCTAAAACCTATGTCCAACATGTGATGGAGCAGGAT
GGAAAAAAATTGATCGAGCTGTTGGATCAGGGCGCGCATTTTTACATTTGCGGGGAT
GGTTCGCAGATGGCACCCGCCGTGGAGGCCACCCTTATGAAAAGCTATGCAGATGTG
CACCAGGTAAGCGAAGCGGATGCCCGTCTGTGGCTGCAACAGTTGGAAGAAAAAGGT
CGCTATGCAAAAGACGTGTGGGCAGGT
```

BIOCATALYST AND METHODS FOR SYNTHESIZING MIXED DISULFIDE CONJUGATES OF THIENOPYRIDINE COMPOUNDS

STATEMENT REGARDING FEDERALLY SPONSORED RESEARCH OR DEVELOPMENT

This invention was made with government support under AA020090 awarded by the National Institutes of Health. The government has certain rights in the invention.

FIELD OF THE INVENTION

The present invention relates to methods for synthesizing mixed disulfide conjugates of thienopyridine compounds with a genetically engineered variant of cytochrome P450 BM3 or CYP102A1 as a catalyst, and belongs to the field of chemical synthesis.

INTRODUCTION

Mixed disulfide conjugates of thienopyridines are promising antiplatelet agents as demonstrated before (see, e.g., Zhang, H., et al., (2016) J Pharmacol Exp Ther 359, 11-17). These compounds are conjugates of heterocyclic thiols with the active antiplatelet agent of thienopyridines. One of such active antiplatelet agent is the pharmacological active metabolite (AM) of clopidogrel, (Z)-2-(1-((S)-1-(2-chlorophenyl)-2-methoxy-2-oxoethyl)-4-mercaptopiperidin-3-ylidene) acetic acid

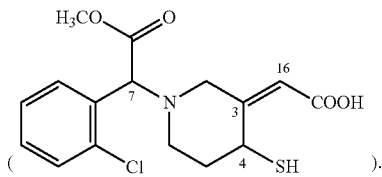 [SMILES: COC(=O)C(c1ccccc1Cl)N1CCC(S)/C(=C\C(=O)O)C1]

Formation of disulfide bond between the AM and heterocyclic thiol yields stable mixed disulfide conjugate that can be readily activated in vivo resulting in fast and efficacious inhibition of platelet aggregation (see, e.g., Zhang, H., et al., (2016) J Pharmacol Exp Ther 359, 11-17; Zhang, H., et al., (2014) Thromb. Haemost. 112, 1304-1311).

In spite of its excellent antiplatelet properties, chemical synthesis of the active metabolites of thienopyridine compounds and their disulfide conjugates has been challenging (see, e.g., Asai, F., Sugidachi, K., Ikeda, T., Iwabuchi, H., Kuroki, Y., Inoue, T., Iwamura, R., and Shinbakawa, N. (2003) Cyclic amino compounds. (Office, U. P. a. T. ed., Sankyo Company, Limited, US; Shaw, S. A., et al., (2015) J Org Chem 80, 7019-7032). Chemical synthesis of these compounds involves multiple steps with low yield. This is at least in part due to: 1) instability of the AM at room temperature. 2) existence of multiple chiral centers. In the case of the AM of clopidogrel, it contains two chiral centers at C4 and C7 in addition to a double bond at C3-16, resulting in a combination of eight stereoisomers. Only 7S and cis double configuration of the AM possesses antiplatelet activity. However, the efficiency of converting trans to cis configuration is very low (see, e.g., Asai, F., Sugidachi, K., Ikeda, T., Iwabuchi, H., Kuroki, Y., Inoue, T., Iwamura, R., and Shinbakawa, N. (2003) Cyclic amino compounds. (Office, U. P. a. T. ed., Sankyo Company, Limited, US).

It has been previously shown that metabolism of thienopyridine compounds in liver microsomes (LM) produces the AM and its mixed disulfide conjugates (see, e.g., Zhang, H., et al., (2014) Thromb. Haemost. 112, 1304-1311). However, use of liver microsomes for large scale synthesis is prohibitory expense due to low product yield and high cost of LM. In fact there is no viable method to produce large quantities of mixed disulfide conjugate of thienopyridine compounds for drug development and other applications.

Accordingly, improved methods for producing large quantities of mixed disulfide conjugate of thienopyridine compounds for drug development and other applications are needed.

The present invention addresses this need.

SUMMARY OF THE INVENTION

Clopidogrel (PLAVIX™), ticlopidine (TICLID™) and prasugrel (EFFIENT™) belong to a class of thienopyridinyl compounds widely used as antiplatelet agents to prevent heart attack and stroke. However, several serious drawbacks have been associated with these drugs including variable response, toxicity and increased risk of bleeding. These drawbacks are closely related to the fact that they are all prodrugs that require oxidative bioactivation by polymorphic cytochromes P450 enzymes (P450s).

To overcome drawbacks associated with thienopyridine compounds (Clopidogrel (PLAVIX™), ticlopidine (TICLID™) and prasugrel (EFFIENT™)), the present invention provides mixed disulfide conjugates of thienopyridine compounds. It is contemplated that such mixed disulfide conjugates of thienopyridine compounds of the present invention are capable of producing active thienopyridine metabolites (e.g., active thienopyridine metabolites capable of antiplatelet activity) in the presence of endogenous glutathione (GSH) without the need for bioactivation by P450s. This approach not only bypasses the oxidative bioactivation process by P450s, but circumvents many of the drawbacks associated with thienopyridinyl drugs. For example, it is contemplated that the mixed disulfide conjugates of thienopyridine compounds of the present invention improve dosing consistency because production of the active metabolite from the conjugates is predictable. In addition, it is contemplated that use of the mixed disulfide conjugates of thienopyridine compounds of the present invention as antiplatelet agents reduce the toxicity as toxic reactive metabolites will not be produced by the thiol-exchange reaction. In addition, the therapeutic onset time for the mixed disulfide conjugates of thienopyridine compounds of the present invention is shortened, which greatly benefits patients who experience acute cardiovascular events. For example, the standard regimen for clopidogrel requires continuously dosing patients for 3-5 days as only a small percentage of the ingested drug are converted to the active metabolite. In contrast, it is contemplated that the mixed disulfide conjugates of thienopyridine compounds of the present invention will release the active metabolites with high yields in less than 30 min. In addition, it is contemplated that the mixed disulfide conjugates of thienopyridine compounds of the present invention will have superior stability over the active metabolites and therefore can be used to quantitatively generate the active metabolites for basic and clinical research in vitro.

Accordingly, the present invention relates to a process for efficiently synthesizing highly optically active mixed disulfide conjugates of thienopyridine compounds with genetically engineered biocatalysts, i.e., a one-step process for preparing highly optically active mixed disulfide conjugates of thienopyridine compounds by mixing 2-oxo thienopyridine and heterocyclic thiols in the presence of reducing reagent NADPH or NADH and a genetically engineered variant of cytochrome P450 BM3 or CYP102A1 as a catalyst. The operation of the process is simple, and the raw materials and reagents are readily available. The methods selectively produce the cis stereoisomer of the conjugates at a higher yield than prior art methods.

In certain embodiments, the present invention provides a mutant CYP102A1 enzyme capable of catalyzing conjugation between 2-oxo thienopyridine and heterocyclic thiols in the presence of a reducing reagent. In some embodiments, the catalyzing of conjugation between 2-oxo thienopyridine and heterocyclic thiols in the presence of a reducing reagent results in the generation of mixed disulfide conjugates of thienopyridine compounds. In some embodiments, the catalyzing of conjugation between 2-oxo thienopyridine and heterocyclic thiols in the presence of a reducing reagent selectively generates cis stereoisomers of the mixed disulfide conjugates of thienopyridine compounds. In some embodiments, the reducing agent is NADPH or NADH.

In some embodiments, the enzyme comprises an amino acid sequence having 85% homology with the wild type amino acid sequence for BM3 (SEQ ID NO: 2; FIG. 4B). In some embodiments, the enzyme comprises an amino acid sequence having 90% homology with the wild type amino acid sequence for BM3 (SEQ ID NO: 2; FIG. 4B). In some embodiments, the enzyme comprises an amino acid sequence having 95% homology with the wild type amino acid sequence for BM3 (SEQ ID NO: 2; FIG. 4B). In some embodiments, the enzyme comprises an amino acid sequence having 99% homology with the wild type amino acid sequence for BM3 (SEQ ID NO: 2; FIG. 4B). In some embodiments, the enzyme comprises an amino acid sequence having one or more of the following amino acid mutations within SEQ ID NO: 2: A82F, L188Q, R47L, F87V, T365N, H116Q, K31T, S56R, A135S, V299D, I458F, P481H, and W1046A. In some embodiments, the enzyme comprises an amino acid sequence having a specific set of mutations recited in Table 2.

In some embodiments, the enzyme comprises nucleic acid having at least 85% homology with SEQ ID NO: 1 (wild type cDNA for BM3; FIG. 4A). In some embodiments, the enzyme comprises nucleic acid having at least 90% homology with SEQ ID NO: 1 (wild type cDNA for BM3; FIG. 4A). In some embodiments, the enzyme comprises nucleic acid having at least 95% homology with SEQ ID NO: 1 (wild type cDNA for BM3; FIG. 4A). In some embodiments, the enzyme comprises nucleic acid having at least 99% homology with SEQ ID NO: 1 (wild type cDNA for BM3; FIG. 4A).

In some embodiments, the enzyme comprises nucleic acid having at least 85% homology with SEQ ID NO: 3 (a variant BM3 cDNA; FIG. 4C). In some embodiments, the enzyme comprises nucleic acid having at least 90% homology with SEQ ID NO: 3 (a variant BM3 cDNA; FIG. 4C). In some embodiments, the enzyme comprises nucleic acid having at least 95% homology with SEQ ID NO: 3 (a variant BM3 cDNA; FIG. 4C). In some embodiments, the enzyme comprises nucleic acid having at least 99% homology with SEQ ID NO: 3 (a variant BM3 cDNA; FIG. 4C). In some embodiments, the enzyme comprises nucleic acid having at least 100% homology with SEQ ID NO: 3 (a variant BM3 cDNA; FIG. 4C).

In certain embodiments, the present invention provides methods for synthesizing cis stereoisomers of mixed disulfide conjugates of thienopyridine compounds, comprising mixing a 2-oxo thienopyridine moiety, a heterocyclic thiol moeity, and the described mutant CYP102A1 enzyme in the presence of a reducing reagent. In some embodiments, the reducing agent is NADPH or NADH. In some embodiments, the 2-oxo thienopyridine moiety is represented by

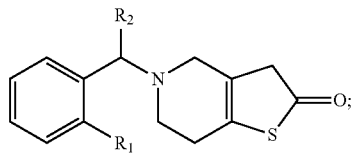

wherein R1 is either Chlorine or Fluorine; wherein R2 is H, COOCH3, or COCHCH2CH2. In some embodiments, the heterocyclic thiol moiety is represented by R3-SH; wherein R3 is selected from 3-nitropyridine-2-thiol, 2-mercaptopyridine, 2-mercapto-6-methylpyridine, 5-chloropyridine-2-thiol, 2-mercapto-5-trifluoromethyl-pyridine, 3-(trifluoromethyl) pyridine-2-thiol, 2-mercaptopyridine-3-carbonitrile, 4,6-dimethyl-2-thioxo-1,2-dihydropyridine-3-carbonitrile, 2-quinolinethiol, 1-amino-3-mercaptoisoquinoline, 6-chloropyridazine-3-thiol, and 2,5-dimethylfuran-3-thiol. In some embodiments, the mixing occurs at ambient temperature. In some embodiments, the mixing occurs for a time period between twenty and sixty minutes. In some embodiments, the mutant CYP102A1 enzyme is comprised within a bacterial cytosolic fraction. In some embodiments, the amount of mutant CYP102A1 enzyme is between approximately 0.1 and 1 µM. In some embodiments, the mixing results in the generation of approximately 100 mg of cis stereoisomers of mixed disulfide conjugates of thienopyridine compounds per liter of the 2-oxo thienopyridine moiety, the heterocyclic thiol moiety, the mutant CYP102A1 enzyme, and the reducing agent.

In certain embodiments, the present invention provides a kit comprising a 2-oxo thienopyridine moiety, a heterocyclic thiol moeity, and one or more of the described mutant CYP102A1 enzymes.

In some embodiments, the kit further comprises a reducing reagent. In some embodiments, the reducing agent is NADPH or NADH. In some embodiments, the 2-oxo thienopyridine moiety is represented by

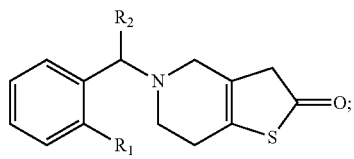

wherein R1 is either Chlorine or Fluorine; wherein R2 is H, COOCH3, or COCHCH2CH2. In some embodiments, the heterocyclic thiol moiety is represented by R3-SH; wherein R3 is selected from 3-nitropyridine-2-thiol, 2-mercaptopyridine, 2-mercapto-6-methylpyridine, 5-chloropyridine-2-thiol, 2-mercapto-5-trifluoromethyl-pyridine, 3-(trifluoromethyl) pyridine-2-thiol, 2-mercaptopyridine-3-carbonitrile, 4,6-dimethyl-2-thioxo-1,2-dihydropyridine-3-carbonitrile, 2-quinolinethiol, 1-amino-3-mercaptoisoquinoline, 6-chloropyridazine-3-thiol, and 2,5-dimethylfuran-3-thiol.

In certain embodiments, the present invention provides a pharmaceutical composition comprising a compound generated with the described method and a pharmaceutically acceptable carrier. In some embodiments, wherein the pharmaceutical composition is configured for intravenous administration.

In certain embodiments, the present invention provides methods of treating, ameliorating, or preventing a cardiovascular disease in a patient comprising administering to said patient a therapeutically effective amount of a compound generated with the described methods. In some embodiments, the administration is selected from the group consisting of oral administration and intravenous administration. In some embodiments, the cardiovascular disease is selected from the group consisting of coronary artery disease, peripheral vascular disease, atherothrombosis, and cerebrovascular disease. In some embodiments, the compound reduces aggregation of platelets. In some embodiments, the reduces aggregation of said platelets occurs through irreversible binding to $P2Y_{12}$ receptors. In some embodiments, the reduces aggregation of said platelets occurs through blocking ADP receptors. In some embodiments, the method further comprises co-administration of at least one agent selected from the group consisting of a HMG-CoA reductase inhibitor, an ACE Inhibitor, a Calcium Channel Blocker, a Platelet Aggregation Inhibitor, a Polyunsaturated Fatty Acid, Fibric Acid Derivative, a Bile Acid Sequestrant, an Antioxidant, a Thrombolytic Agent, and an Antianginal Agent.

BRIEF DESCRIPTION OF THE DRAWINGS

FIG. 4A: Wild Type cDNA of 1541 to 4690 of wild-type B.megaterium cytochrome P-450: NADPH-P-450 reductase gene (see,e.g., Accession J04832) (SEQ ID NO: 1).

FIG. 4B: Wild type amino acid sequence for B.megaterium cytochrome P-450:NADPH-P-450 reductase gene (see, e.g., Accession J04832) (SED ID NO: 2).

FIG. 4C: Optimized cDNA for genetically engineered variant of cytochrome P450 BM3 or CYP102A1 (SEQ ID NO: 3).

DETAILED DESCRIPTION OF THE INVENTION

Figure 1:
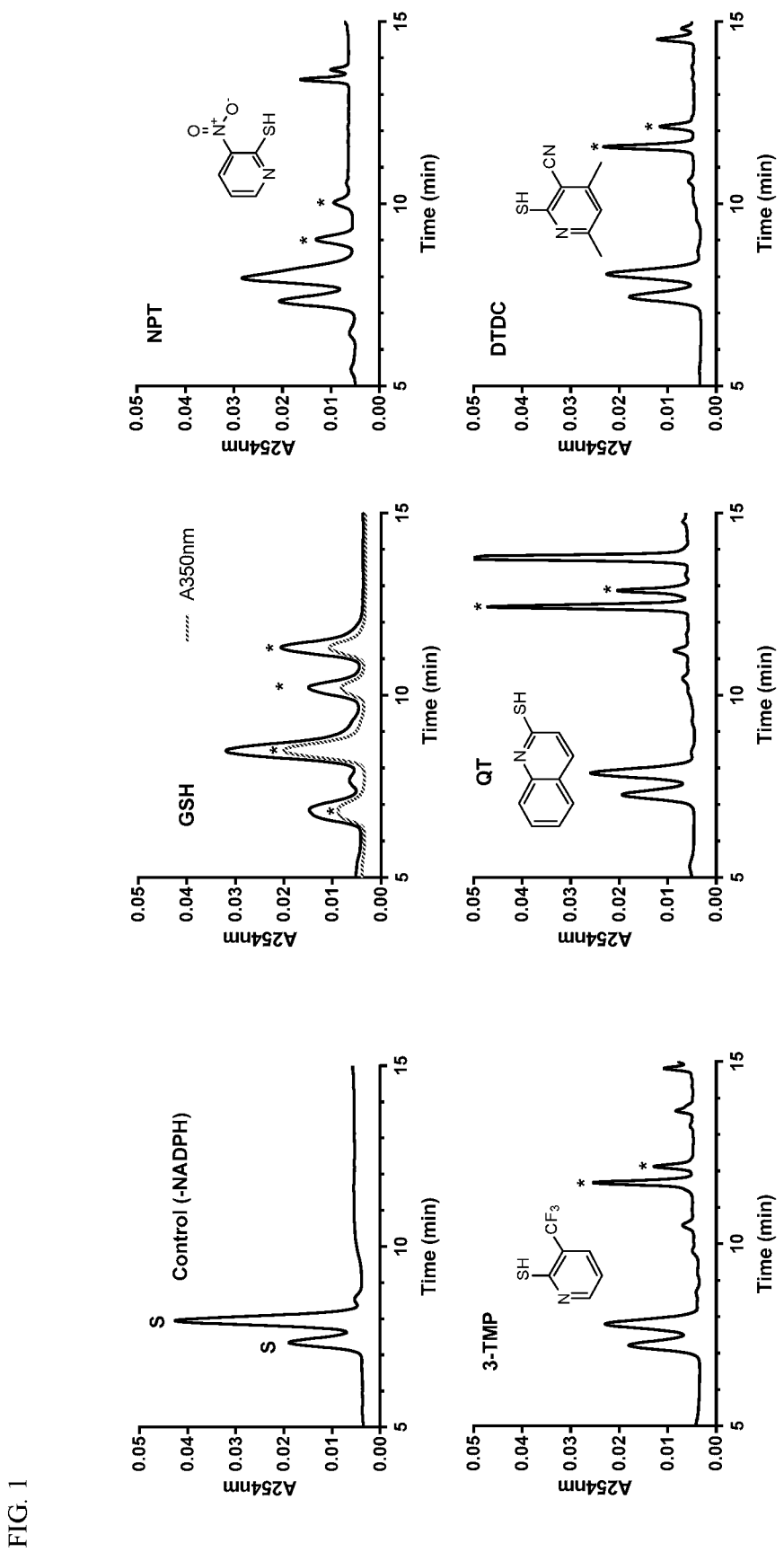
FIG. 1: HPLC analyses of products of mixed disulfide conjugate of clopidogrel. The reaction was performed by mixing 2-oxoclopidogrel, heterocyclic thiol, BM3 and NADPH at 25° C. for 20 min. The reaction was then quenched with equal volume of acetonitrile containing 1% formic acid. Aliquots of 5 µl of the reaction mixture were analyzed by HPLC. The double peak denoted as "S" are the two stereoisomers of rac-2-oxoclopidogrel, whereas the peaks denoted by asterisks represent expected products. Elution was observed at 254 nm.

The present invention relates to a genetically engineered variant of cytochrome P450 BM3 or CYP102A1 as a catalyst, methods for synthesizing mixed disulfide conjugates of thienopyridine compounds with the biocatalyst, and related therapeutics for the treatment, amelioration, and prevention of cardiovascular diseases.

Experiments conducted during the course of developing embodiments for the present invention identified methods for stereo-selective and efficient synthesis of mixed disulfide conjugate of thienopyridine compounds using engineered variants of cytochrome P450 BM3 or CYP102A1 as biocatalyst.

Accordingly, the present invention relates to a process for efficiently synthesizing highly optically active mixed disulfide conjugates of thienopyridine compounds with genetically engineered biocatalysts, i.e., a one-step process for preparing highly optically active mixed disulfide conjugates of thienopyridine compounds by mixing 2-oxo thienopyridine and heterocyclic thiols in the presence of a reducing reagent (e.g., NADPH or NADH) and a genetically engineered variant of cytochrome P450 BM3 or CYP102A1 as a catalyst. The operation of the process is simple, and the raw materials and reagents are readily available. The methods selectively produce the cis stereoisomer of the conjugates at a higher yield than prior art methods (e.g., produces cis stereoisomer of the conjugates at a yield much superior than use of liver microsomes).

Biological enzyme catalysts, such as $P450_{BM-3}$ enzymes, find increasing use in a variety of industrial applications, ranging from synthesis of fine chemicals, intermediates, pharmaceuticals and drug metabolites to degradation of organic chemical contaminants and pollutants. Protein engineering, using directed evolution or site-directed mutagenesis, can be used to isolate variants of known enzymes, which may create new opportunities and applications for their catalytic activities.

$P450_{BM-3}$ from *Bacillus megaterium* (see, e.g., Miura, Y., and Fulco, A. J. (1975) Biochim. Biophys. Acta 388, 305-317) belongs to the superfamily of cytochrome P450 enzymes. There are over 7,700 genes encoding P450 enzymes in the various gene sequence databases. Nomenclature of P450 enzymes has been systemized. The superfamily of enzymes are referred to as CYP, followed by a number for a family of enzymes (hence CYP1, CYP51, CYP102, etc.) which are divided into subfamilies denoted by alphabets (hence CYP1A, CYP101B, etc.) and each sub-family member is denoted by a number (hence CYP1A1, CYP3A4, CYP101D3, etc.). A gene encoding a CYP enzyme is denoted by italics, e.g. CYP101A1 gene. $P450_{BM-3}$ has been designated CYP102A1, i.e. it is the first member of the CYP102 family. Henceforth the systemic name of CYP102A1 will be used for $P450_{BM-3}$.

CYP102A1 (see, e.g., Miura, Y., and Fulco, A. J. (1975) Biochim. Biophys. Acta 388, 305-317) is an attractive enzyme for biotransformation applications because it is catalytically self-sufficient. Unlike other P450 enzymes, in which the P450 monooxygenase and the electron transfer co-factor proteins are separate entities, CYP102A1 has the haem monooxygenase domain fused to the diflavin electron transfer reductase domain, which contains both the FAD and FMN prosthetic groups in a single polypeptide. The natural substrates of CYP102A1 are believed to be linear or branched medium chain fatty acids (see, e.g., Miura, Y., and Fulco, A. J. (1975) Biochim. Biophys. Acta 388, 305-317; Cryle, M. J., et al., (2006) Chem Commun, 2353-2355). The crystal structure of the CYP102A1 haem domain became available in 1993 (see, e.g., Ravichandran, K. G., et al., (1993) Science 261, 731-736), revealing the active site structure and the presence of a substrate access channel. The crystal structure with a bound substrate indicated a change in the side chain conformation for F87 upon substrate binding (see, e.g., Li, H., and Poulos, T. L. (1997) Nature Struct. Biol. 4, 140-146).

CYP102A1 from *Bacillus megaterium* is a self-sufficient and highly efficient enzyme for hydroxylating fatty acids. Various variants of CYP102A1 have been found to oxidize small molecules other than fatty acids with enhanced activities. However there is no application for stereo-selective synthesis of heterocyclic conjugates of thienopyridin compounds.

Experiments conducted during the course of developing embodiments for the present invention developed a method that produces cis stereoisomer of the conjugates at a yield much superior than use of liver microsomes. The reaction involved mixing bacterial cytosolic fraction containing BM3 variants (0.1-1 µM), 2-oxo thienopyridine, heterocyclic thiols, and NADPH or NADH, followed by incubation for 20-60 min. In the presence of desired heterocyclic thiols, the method produced the conjugate with cis configuration only at yields as high as 100 mg per liter of reaction mixture.

As such, in certain embodiments, the present invention provides variants of CYP102A1. In some embodiments, the variants of CYP102A1 are optimized for use as biocatalysts within methods for synthesizing mixed disulfide conjugates of thienopyridine compounds. Indeed, experiments described herein resulted in optimized gene expression of CYP102A1 by re-designing the cDNA of CYP102A1. The re-designed cDNA optimize codon usage for over-expression in bacteria and eliminates structural barriers for transcription. The optimized cDNA is shown in SEQ ID NO: 3 and encodes 1054 amino acid residues including a hexaHis tag at N-terminus for affinity purification. In preferred embodiments, the sequence may be at least 55%, 65%, 80% or 90% and more preferably at least 95%, 97% or 99% homologous thereto over at least 20, preferably at least 30, for instance at least 40, 60, 100, 200, 300, 400 or more contiguous amino acids, or even over the entire sequence of the homologue. In some embodiments, the CYP102A1 biocatalyst may have a percentage identity with SEQ ID NO: 3 which is the same as any of the specific percentage homology values (i.e. it may have at least 40%, 55%, 80% or 90% and more preferably at least 95%, 97% or 99% identity) across any of the lengths of SEQ ID NO: 3.

The homologous sequence may represent a mutated portion of the CYP102A1 sequence (SEQ ID NO: 3) and/or may be present in the form of the full-length fused polypeptide of the biocatalyst.

In some embodiments, the CYP102A1 or BM3 variant comprises an amino acid sequence having 85% homology with the wild type amino acid sequence for BM3 (SEQ ID NO: 2; FIG. 4B). In some embodiments, the BM3 variant comprises an amino acid sequence having 90% homology with the wild type amino acid sequence for BM3 (SEQ ID NO: 2; FIG. 4B). In some embodiments, the BM3 variant comprises an amino acid sequence having 95% homology with the wild type amino acid sequence for BM3 (SEQ ID NO: 2; FIG. 4B). In some embodiments, the BM3 variant comprises an amino acid sequence having 99% homology with the wild type amino acid sequence for BM3 (SEQ ID NO: 2; FIG. 4B). In some embodiments, the BM3 variant comprises an amino acid sequence having one or more of the following amino acid mutations within SEQ ID NO: 2: A82F, L188Q, R47L, F87V, T365N, H116Q, K31T, S56R, A135S, V299D, I458F, P481H, and W1046A. In some embodiments, the BM3 variant comprises an amino acid sequence having a specific set of mutations recited in Table 2.

In some embodiments, the BM3 variant comprises nucleic acid having at least 85% homology with SEQ ID NO: 1 (wild type cDNA for BM3; FIG. 4A). In some embodiments, the BM3 variant comprises nucleic acid having at least 90% homology with SEQ ID NO: 1 (wild type cDNA for BM3; FIG. 4A). In some embodiments, the BM3 variant comprises nucleic acid having at least 95% homology with SEQ ID NO: 1 (wild type cDNA for BM3; FIG. 4A). In some embodiments, the BM3 variant comprises nucleic acid having at least 99% homology with SEQ ID NO: 1 (wild type cDNA for BM3; FIG. 4A).

In some embodiments, the BM3 variant comprises nucleic acid having at least 85% homology with SEQ ID NO: 3 (a variant BM3 cDNA; FIG. 4C). In some embodiments, the BM3 variant comprises nucleic acid having at least 90% homology with SEQ ID NO: 3 (a variant BM3 cDNA; FIG. 4C). In some embodiments, the BM3 variant comprises nucleic acid having at least 95% homology with SEQ ID NO: 3 (a variant BM3 cDNA; FIG. 4C). In some embodiments, the BM3 variant comprises nucleic acid having at least 99% homology with SEQ ID NO: 3 (a variant BM3 cDNA; FIG. 4C). In some embodiments, the BM3 variant comprises nucleic acid having at least 100% homology with SEQ ID NO: 3 (a variant BM3 cDNA; FIG. 4C).

Any of the homologous proteins (i.e. described as being homologous to another protein) mentioned herein are typically at least 40% homologous to the relevant protein.

Homology can be measured using known methods. For example the UWGCG Package provides the BESTFIT program which can be used to calculate homology (for example used on its default settings) (Devereux et al (1984) Nucleic Acids Research 12, 387-395). The PILEUP and BLAST algorithms can be used to calculate homology or line up sequences (typically on their default settings), for example as described in Altschul S. F. (1993) J Mol Evol 36:290-300; Altschul, S, F et al (1990) J Mol Biol 215:403-10.

The biocatalytic or enzymatic activity of the variant CYP102A1 enzyme of the invention is typically measured in vitro using any of the substrates or conditions mentioned herein and is given as the NADPH oxidation rate, the product formation rate and coupling efficiency. The rates are turnover frequencies and given in (nmol NADPH) (nmol CYP102A1)$^{-1}$ (min)$^{-1}$ or (nmol product) (nmol CYP102A1)$^{-1}$ (min)$^{-1}$. Coupling efficiency is the percentage of NADPH consumed which was utilised for product formation, i.e. a percentage of the theoretical maximum efficiency. The CYP102A1 enzyme of the invention (for example when used in the synthetic methods of the invention) may typically have a coupling efficiency of at least 1%, such as at least 2%, 4%, 6%, 10%, 20%, 40%, 80% or more. The CYP102A1 enzyme (for example when used in the methods of the invention) typically has a product formation rate of at least 2 min$^{-1}$, such as at least 4, 10, 15, 20, 25, 50, 100, 200, 300, 500, 700, 1000, 2000 min$^{-1}$ or more. Where more than one product is formed (which is commonly the case), the product formation rates represent the total amount of all oxidation products formed. In some embodiments, product formation rate of a specific oxidation product is measured, i.e. not all oxidation products may be measured.

The variant CYP102A1 biocatalyst described herein (SEQ ID NO: 3 and variants thereof; any of the mutants recited in Table 2) are generally introduced into the wild type enzyme by using methods known in the art, such as site directed mutagenesis of the enzyme, PCR and gene shuffling methods or by the use of multiple mutagenic oligonucleotides in cycles of site-directed mutagenesis. Thus the mutations may be introduced in a directed or random manner. The mutagenesis method thus produces one or more polynucleotides encoding one or more different mutants. Typically a library of mutant genes is produced which can be used to produce a library of mutant enzymes.

The enzyme may have 1, 2, 3, 4, 5 to 10, 10 to 20, 20 to 40 or more other mutations in addition to the one or more mutations specified in SEQ ID NO: 3 and Table 2, such as substitutions, insertions or deletions. These additional mutations may or may not enhance the biocatalytic activity within methods for stereo-selective and efficient synthesis of mixed disulfide conjugate of thienopyridine compounds. An insertion will typically be N and/or C terminal. Thus the enzyme may contain a short peptide of up to 20 amino acids or a full-length protein fused to either or both of the termini, e.g. to aid protein purification by affinity chromatography or immobilisation on a solid matrix. A deletion typically comprises the deletion of amino acids which are not involved in catalysis, such as those outside the active site (thus the enzyme is a mutated fragment of a naturally occurring enzyme).

When used within methods for synthesis of mixed disulfide conjugate of thienopyridine compounds the variant CYP102A1 biocatalyst of the invention results in stereo-selective and efficient synthesis with respect to the methods not utilizing such a biocatalyst. The substrate for the oxidation process catalyzed the variant CYP102A1 biocatalyst is any organic compound, more typically any organic compound capable of being oxidized by a monooxygenase enzyme. The oxidation process causes the formation of a C=O bond in the compound, generally as the alcohol from the oxidation of a carbon-hydrogen bond, but an epoxide may be formed from the oxidation of a C=C bond. The oxidation may thus introduce an alcohol, aldehyde, ketone or epoxide group. Alternatively the oxidation may cause the further oxidation of an oxygen containing group, such as converting an alcohol group into an aldehyde or ketone. 1, 2 or more carbon atoms may be attacked in the same substrate molecule. Oxidation can also result in N- and O-dealkylation of the substrate molecule.

The oxidation typically gives rise to 1, 2 or more oxidation products. These different products may result from different carbon atoms being attacked and/or from different degrees of oxidation occurring at a given carbon atom.

The oxidation may occur on either a ring carbon atom or a substituent carbon atom or both. At least the initial oxidation will involve attack of a C—H bond which may be activated or non-activated or attack at a carbon-carbon double bond (typically giving an epoxide). Generally an activated C—H bond is where the carbon atom is in a benzylic or allylic position. Aromatic rings and olefinic double bonds activate C—H bonds to attack by stabilizing the radical intermediate or any build-up of charge generated during the reaction pathway. The carbon of the C—H bond may be primary, secondary or tertiary. The oxidation may occur to result in dehydrogenation leading to a C=C double bond formation rather than insertion of an oxygen atom. This is most likely to occur when the alkyl substituent is branched, or dehydrogenation leads to a C=C bond that is conjugated to an aromatic system, or dehydrogenation leads to the formation of an aromatic system. The process is typically carried out in the presence of the variant CYP102A1 enzyme, the substrate and the natural co-factors of the enzyme which are NADPH or NADH and dioxygen.

In some embodiments, the variant CYP102A1 enzyme (SEQ ID NO: 3 and variants thereof; any of the mutants recited in Table 2) is expressed within a cell. Typically the cell is one in which the variant CYP102A1 enzyme (SEQ ID NO: 3; Table 2) or wild type CYP102A1 does not naturally occur. In another embodiment the variant CYP102A1 enzyme (SEQ ID NO: 3; Table 2) is expressed in a cell in which wild type CYP102A1 does naturally occur, but at higher levels than naturally occurring levels. The cell may produce 1, 2, 3, 4 or more different variant CYP102A1 enzymes of the invention.

The cell may be prokaryotic or eukaryotic and is generally any of the cells or of any of the organisms mentioned herein. Preferred cells are *Escherichia coli*, *Pseudomonas* sp., flavobacteria or fungi cells (e.g. *Aspergillus* and yeast, especially *Pichia* sp.). Also contemplated for use according to the invention are *Rhodococcus* sp. and *Bacillus* sp. The cell may or not be one which in its naturally occurring form is able to oxidize any of the substrates or generate any of the oxidation products mentioned herein. Typically the cell is in a substantially isolated form and/or substantially purified form, in which case it will generally comprise at least 90%, e.g. at least 95%, 98% or 99% of the cells or dry mass of the preparation.

The cell is typically produced by introducing into a cell (i.e. transforming the cell with) a vector comprising a polynucleotide that encodes the variant CYP102A1 enzyme of the invention. It is to be understood that due to the degeneracy of the nucleotide code, more than one polynucleotide can encode each of the variant CYP102A1 enzymes of the invention. It is also to be understood that the nucleotide sequence may be engineered to exhibit a codon bias suitable for a particular cell or organism. The vector may integrate into the genome of the cell or remain extra-chromosomal. The cell may develop into the animal or plant discussed below. Typically the coding sequence of the polynucleotide is operably linked to a control sequence which is capable of providing for the expression of the coding sequence by the host cell. The control sequence is generally a promoter, typically of the cell in which the monooxygenase is expressed.

The term "operably linked" refers to a juxtaposition wherein the components described are in a relationship permitting them to function in their intended manner. A control sequence "operably linked" to a coding sequence is ligated in such a way that expression of the coding sequence is achieved under conditions compatible with the control sequences.

The vector is typically a transposon, plasmid, virus or phage vector. It typically comprises an origin of replication. It typically comprises one or more selectable marker genes, for example an ampicillin resistance gene in the case of a bacterial plasmid. The vector is typically introduced into host cells using conventional techniques including calcium phosphate precipitation, DEAE-dextran transfection, or electroporation.

Accordingly, the present invention relates to a process for efficiently synthesizing highly optically active mixed disulfide conjugates of thienopyridine compounds with genetically engineered biocatalysts, i.e., a one-step process for preparing highly optically active mixed disulfide conjugates of thienopyridine compounds by mixing 2-oxo thienopyridine and heterocyclic thiols in the presence of a reducing reagent (e.g., NADPH or NADH) and the described genetically engineered variant of cytochrome P450 BM3 or CYP102A1 as a catalyst.

In certain embodiments, the present invention provides methods for stereo-selective and efficient synthesis of mixed disulfide conjugate of thienopyridine compounds using a variant CYP102A1 (BM3) enzyme (SEQ ID NO: 3; Table 2) as biocatalyst. In some embodiments, the method includes a process shown in the following reaction scheme:

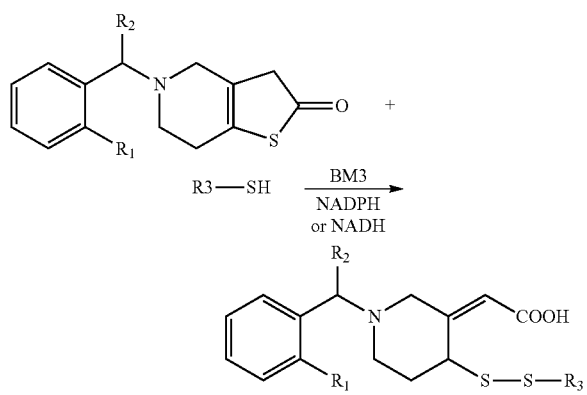

R1, Cl or F
R2 = H, —COOCH3, —COCHCH2CH2
R3 = heterocyclic thiol

The synthetic reaction, as depicted in the above reaction scheme, proceeds by mixing reactants 2-oxo thienopyridine and heterocyclic thiols in the presence of reducing reagent NADPH or NADH and a variant CYP102A1 (BM3) enzyme (SEQ ID NO: 3; Table 2) as biocatalyst. The reaction does not require any special reactors and apparatus, nor does it require high temperature and pressure usually needed for chemical synthesis. The reaction goes to completion at ambient temperature (e.g., room temperature) in less than 60 min.

In some embodiments, the reaction involves mixing bacterial cytosolic fractions comprising BM3 variants (0.1-1 µM), 2-oxo thienopyridine, heterocyclic thiols, and NADPH or NADH, followed by incubation for 20-60 min. In the presence of desired heterocyclic thiols, the method produces the conjugate with cis configuration only at yields as high as 100 mg per liter of reaction mixture.

Such methods result in the synthesis of substantially enantiomerically pure compositions and pharmaceutical compositions comprising mixed disulfide conjugates of thienopyridine compounds. Indeed, the methods are capable of producing the cis stereoisomer forms of the conjugates at a high yield.

Within the reaction scheme, the heterocyclic thiol is not limited to a specific chemical moiety for R3. In some embodiments, R3 is any chemical moiety that renders the resulting compound capable of producing active thienopyridine metabolites upon interaction with endogenous glutathione (GSH) (e.g., active thienopyridine metabolites capable of antiplatelet activity). In some embodiments, R3 is any chemical moiety that renders the resulting compound capable of treating, ameliorating, or preventing cardiovascular disorders (e.g., coronary artery disease, peripheral vascular disease, and cerebrovascular disease) in a patient, such as those that are responsive to antiplatelet agents (such as clopidogrel, ticlopidine, and prasugrel). In some embodiments, R3 is any chemical moiety that renders the resulting compound capable of inhibiting platelet aggregation by, for example, altering the function of platelet membranes by blocking ADP receptors (e.g., thereby preventing a conformational change of glycoprotein IIb/IIIa which allows platelet binding to fibrinogen). In some embodiments, R3 is any chemical moiety that renders the resulting compound capable of reducing aggregation ("clumping") of platelets by irreversibly binding to $P2Y_{12}$ receptors.

Examples of heterocyclic thiol moieties (R3) include, but are not limited to, those shown in Table 1.

TABLE 1

A list of heterocyclic thiols used for reaction with 2-oxoclopidogrel

| Chemical Name | Abbreviation |
|---|---|
| 3-nitropyridine-2-thiol | NPT |
| 2-mercaptopyridine | MP |
| 2-mercapto-6-methylpyridine | MMP |
| 5-chloropyridine-2-thiol | 5-CPT |
| 2-mercapto-5-trifluoromethyl-pyridine | 5-TMP |
| 3-(trifluoromethyl)pyridine-2-thiol | 3-TMP |
| 2-mercaptopyridine-3-carbonitrile | MPC |
| 4,6-dimethyl-2-thioxo-1,2-dihydropyridine-3-carbonitrile | DTDC |
| 2-quinolinethiol | QT |
| 1-amino-3-mercaptoisoquinoline | AMP |
| 6-chloropyridazine-3-thiol | CPT |
| 2,5-dimethylfuran-3-thiol | DFT |

In some embodiments, R3 is selected from

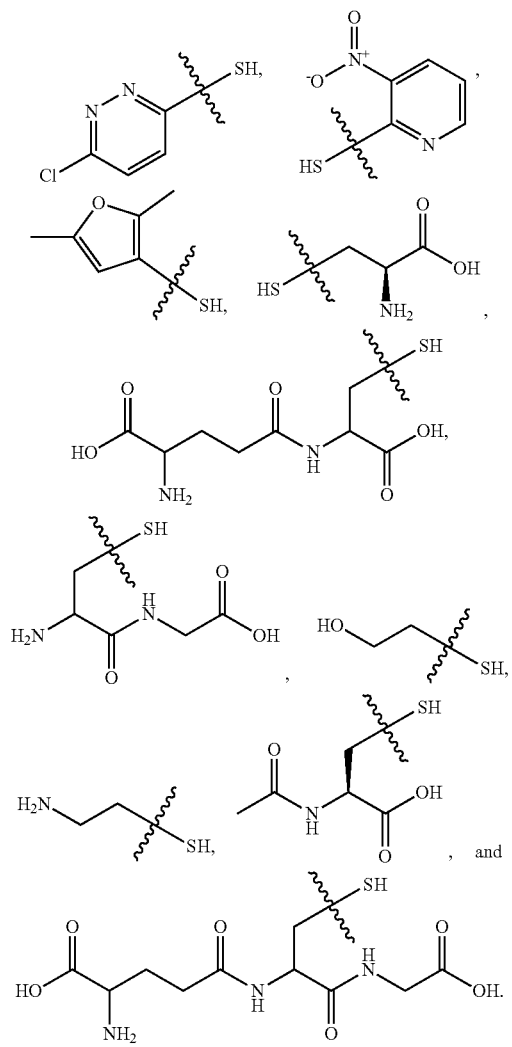

It is contemplated that mixed disulfide conjugates of thienopyridine compounds generated with such methods utilizing the genetically engineered variant of cytochrome P450 BM3 or CYP102A1 as a catalyst will suffice the need for large scale synthesis of the conjugtes for drug development and production because production of the cis stereoisomer of the conjugates is predictably generated at a higher yield than prior art methods. Furthermore the reaction is performed at ambient temperature and atompheric pressure with short reaction time. With the readily availability of synthesized conjugates, it is contemplated that use of the mixed disulfide conjugates of thienopyridine compounds of the present invention as antiplatelet agents will reduce the toxicity because toxic reactive metabolites are not produced by the thiol-exchange reaction. In addition, it is contemplated that the therapeutic onset time for the mixed disulfide conjugates of thienopyridine compounds of the present invention will be shortened, which greatly benefits patients who experience acute cardiovascular events. The standard regimen for clopidogrel requires continuously dosing patients for 3-5 days because only a small percentage of ingested clopidogrel are converted to the active metabolite. In contrast, it is contemplated that the mixed disulfide conjugates of thienopyridine compounds of the present invention can release the active metabolites with high yields in less than 30 min. In addition, it is contemplated that the mixed disulfide conjugates of thienopyridine compounds of the present invention will have superior stability over the active metabolites and therefore they can be used to quantitatively generate the active metabolites for basic and clinical research in vitro.

The invention further relates to methods of treating, ameliorating, or preventing cardiovascular disorders in a patient, such as those that are responsive to antiplatelet agents (such as clopidogrel, ticlopidine, and prasugrel) comprising administering to a patient such mixed disulfide conjugates of thienopyridine compounds (e.g., generated with methods utilizing the genetically engineered variant of cytochrome P450 BM3 or CYP102A1 as a catalyst). Such disorders include, but are not limited to, coronary artery disease, peripheral vascular disease, and cerebrovascular disease. In some embodiments, the mixed disulfide conjugates of thienopyridine compounds are used to inhibit platelet aggregation by, for example, altering the function of platelet membranes by blocking ADP receptors (e.g., thereby preventing a conformational change of glycoprotein IIb/IIIa which allows platelet binding to fibrinogen). In some embodiments, the mixed disulfide conjugates of thienopyridine compounds reduce aggregation ("clumping") of platelets by irreversibly binding to $P2Y_{12}$ receptors. In some embodiments, the mixed disulfide conjugates of thienopyridine compounds are used within pharmaceutical compositions configured for intravenous (IV) administration (e.g., in medical situations requiring IV administration of antiplate agents (e.g., coronary angioplasty)).

In some embodiments, the mixed disulfide conjugates of thienopyridine compounds (e.g., generated with methods utilizing the genetically engineered variant of cytochrome P450 BM3 or CYP102A1 as a catalyst) are used to treat, ameliorate, or prevent cardiovascular disorders in an animal (e.g., a mammalian patient including, but not limited to, humans and veterinary animals), such as those that are responsive to antiplatelet agents (such as clopidogrel, ticlopidine, and prasugrel) comprising administering to a patient a mixed disulfide conjugate of thienopyridine compound of the invention. Such disorders include, but are not limited to, coronary artery disease, peripheral vascular disease, atherothrombosis, and cerebrovascular disease. Indeed, in some embodiments, the mixed disulfide conjugates of thienopyridine compounds (e.g., generated with methods utilizing the genetically engineered variant of cytochrome P450 BM3 or CYP102A1 as a catalyst) are used to decrease platelet aggregation and/or inhibit thrombus formation. In this regard, such diseases and pathologies are amenable to treatment or prophylaxis using the present methods and mixed disulfide conjugates of thienopyridine compounds.

In some embodiments, the mixed disulfide conjugates of thienopyridine compounds (e.g., generated with methods utilizing the genetically engineered variant of cytochrome P450 BM3 or CYP102A1 as a catalyst) are used in the prevention of vascular ischemic events in patients with symptomatic artherosclerosis. In some embodiments, the mixed disulfide conjugates of thienopyridine compounds are used to treat or prevent acute coronary syndrome without ST-segment elevation. In some embodiments, the mixed disulfide conjugates of thienopyridine compounds are used for the prevention of thrombosis after placement of intracoronary stent. In some embodiments, the mixed disulfide conjugates of thienopyridine compounds are used to inhibit platelet aggregation by, for example, altering the function of platelet membranes by blocking ADP receptors (e.g., thereby preventing a conformational change of glycoprotein IIb/IIIa which allows platelet binding to fibrinogen). In some embodiments, the mixed disulfide conjugates of thienopyridine compounds reduce aggregation ("clumping") of platelets by irreversibly binding to $P2Y_{12}$ receptors. In some embodiments, the mixed disulfide conjugates of thienopyridine compounds are used to prolong bleeding time. In some embodiments, the mixed disulfide conjugates of thienopyridine compounds are used to decrease incidence of stroke in high-risk patients.

In some embodiments, the present invention provides pharmaceutical compositions comprising mixed disulfide conjugates of thienopyridine compounds (e.g., generated with methods utilizing the genetically engineered variant of cytochrome P450 BM3 or CYP102A1 as a catalyst) configured for intravenous (IV) administration. In some embodiments, such pharmaceutical compositions comprising mixed disulfide conjugates of thienopyridine compounds configured for intravenous (IV) administration are used in the treatment, amelioration and prevention of atherothrombosis. In some embodiments, such pharmaceutical compositions comprising mixed disulfide conjugates of thienopyridine compounds configured for intravenous (IV) administration are used for rapid inhibition of platelet aggregation. In some embodiments, such pharmaceutical compositions comprising mixed disulfide conjugates of thienopyridine compounds configured for intravenous (IV) administration are used during percutaneous coronary intervention procedures (e.g., coronoary angioplasty) for rapid inhibition of platelet aggregation. Indeed, anti-platelet therapy is at the cornerstone of prevention and treatment of atherothrombosis. Platelet activation by agonists such as plaque rupture and sheer pressure stress from stents plays an important role in the development of atherothrombosis. Under certain clinical situations where patients suffer acute cardiovascular syndromes or undergo percutaneous cardiovascular intervention, rapid and complete inhibition of platelet aggregation is needed to prevent cardiovascular deaths and ischemic complications. Such medical scenarios require intravenous administration of anti-platelet agents that possess short onset time. However, this is still an unmet medical need since the anti-platelet agents currently being used either have slow onset time or cannot be administrated intravenously (see, e.g., Silvain, J., and Montalescot, G., (2012) Circ. Cariovasc. Interv. 5:328-331). The mixed disulfide conjugates of thienopyridine compounds of the present invention fulfill this unmet medical need as such compounds can be administrated both orally and intravenously and possess short onset time.

Some embodiments of the present invention provide methods for administering an effective amount of a mixed disulfide conjugate of a thienopyridine compound of the invention (e.g., generated with methods utilizing the genetically engineered variant of cytochrome P450 BM3 or CYP102A1 as a catalyst) and at least one additional therapeutic agent (including, but not limited to, a therapeutic agent known to treat, ameliorate, or prevent cardiovascular disorders), and/or therapeutic technique (e.g., a surgical intervention). A number of therapeutic agents known to treat, ameliorate, or prevent cardiovascular disorders are contemplated for use in the methods of the present invention. Indeed, the present invention contemplates, but is not limited to, administration of numerous therapeutic agents known to treat, ameliorate, or prevent cardiovascular disorders. Examples include, but are not limited to, HMG-COA reductase inhibitors (e.g., Atorvastatin (LIPITOR™), Pravastatin (PRAVACHOL™), Simvastatin (ZOCOR™), Rosuvastatin (CRESTOR™), Pitavastatin (LIVALO™), Lovastatin (MEVACORIM, ALTOCORIM), Fluvastatin (LESCOL™)), ACE Inhibitors (e.g., Ramipril (ALTACE™), Quinapril (ACCUPRIL™), Captopril (CAPOTEN™), Enalapril (VASOTEC™), Lisinopril (ZESTRIL™)), Calcium Channel Blockers (e.g., Amlodipine (NORVASC™), Nifedipine (PROCARDIA™), Verapamil (CALAN™), Felodipine (PLENDIL™), Diltiazem (CARDIZEM™)), Platelet Aggregation Inhibitors (other than TICLOPIDINE™, CLOPIDOGREL™, and PRASUGREL™) (e.g., Abciximab (REOPRO™), Aspirin, Warfarin (COUMADINIM), HEPARIN™), Polyunsaturated Fatty Acids (e.g., Omega-3 polyunsaturated fatty acid (Fish Oil)), Fibric Acid Derivatives (e.g., Fenofibrate (TRICOR™), Gemfibrozil (LOPID™)), Bile Acid Sequestrants (e.g., Colestipol (COLESTIDIM), Cholestyramine (QUESTRAN™)), Antioxidants (e.g., Vitamin E), Nicotinic Acid Derivatives (e.g., Niacin (NIASPAN™), Thromboytic agents (e.g., Alteplase (ACTIVASE™)), and Antianginal Agents (e.g., Ranolazine (RANEXAIM).

In some embodiments of the present invention, a mixed disulfide conjugate of thienopyridine compound of the invention (e.g., generated with methods utilizing the genetically engineered variant of cytochrome P450 BM3 or CYP102A1 as a catalyst) and one or more additional therapeutic agent is administered to an patient under one or more of the following conditions: at different periodicities, at different durations, at different concentrations, by different administration routes, etc. In some embodiments, the mixed disulfide conjugate of thienopyridine compound is administered prior to the additional therapeutic agent, e.g., 0.5, 1, 2, 3, 4, 5, 10, 12, or 18 hours, 1, 2, 3, 4, 5, or 6 days, or 1, 2, 3, or 4 weeks prior to the administration of the additional therapeutic agent. In some embodiments, the mixed disulfide conjugate of thienopyridine compound is administered after the additional therapeutic agent, e.g., 0.5, 1, 2, 3, 4, 5, 10, 12, or 18 hours, 1, 2, 3, 4, 5, or 6 days, or 1, 2, 3, or 4 weeks after the administration of the additional therapeutic agent. In some embodiments, the mixed disulfide conjugate of thienopyridine compound compound and the additional therapeutic agent are administered concurrently but on different schedules, e.g., the mixed disulfide conjugate of thienopyridine compound is administered daily while the additional therapeutic agent is administered once a week, once every two weeks, once every three weeks, or once every four weeks. In other embodiments, the mixed disulfide conjugate of thienopyridine compound is administered once a week while the additional therapeutic agent is administered daily, once a week, once every two weeks, once every three weeks, or once every four weeks.

Compositions within the scope of this invention include all compositions wherein the mixed disulfide conjugates of thienopyridine compounds of the present invention (e.g., generated with methods utilizing the genetically engineered variant of cytochrome P450 BM3 or CYP102A1 as a catalyst) are contained in an amount which is effective to achieve its intended purpose. While individual needs vary, determination of optimal ranges of effective amounts of each component is within the skill of the art. Typically, the compounds may be administered to mammals, e.g. humans, orally at a dose of 0.0025 to 50 mg/kg, or an equivalent amount of the pharmaceutically acceptable salt thereof, per day of the body weight of the mammal being treated for disorders responsive to induction of apoptosis. In one embodiment, about 0.01 to about 25 mg/kg is orally administered to treat, ameliorate, or prevent such disorders. For intramuscular injection, the dose is generally about one-half of the oral dose. For example, a suitable intramuscular dose would be about 0.0025 to about 25 mg/kg, or from about 0.01 to about 5 mg/kg.

The unit oral dose may comprise from about 0.01 to about 1000 mg, for example, about 0.1 to about 100 mg of the mixed disulfide conjugate of thienopyridine compound. The unit dose may be administered one or more times daily as one or more tablets or capsules each containing from about 0.1 to about 10 mg, conveniently about 0.25 to 50 mg of the compound or its solvates.

In a topical formulation, the compound may be present at a concentration of about 0.01 to 100 mg per gram of carrier. In a one embodiment, the mixed disulfide conjugate of thienopyridine compound compound is present at a concentration of about 0.07-1.0 mg/ml, for example, about 0.1-0.5 mg/ml, and in one embodiment, about 0.4 mg/ml.

In addition to administering the mixed disulfide conjugate of thienopyridine compound as a raw chemical, the compounds of the invention may be administered as part of a pharmaceutical preparation containing suitable pharmaceutically acceptable carriers comprising excipients and auxiliaries which facilitate processing of the compounds into preparations which can be used pharmaceutically. The preparations, particularly those preparations which can be administered orally or topically and which can be used for one type of administration, such as tablets, dragees, slow release lozenges and capsules, mouth rinses and mouth washes, gels, liquid suspensions, hair rinses, hair gels, shampoos and also preparations which can be administered rectally, such as suppositories, as well as suitable solutions for administration by intravenous infusion, injection, topically or orally, contain from about 0.01 to 99 percent, in one embodiment from about 0.25 to 75 percent of active compound(s), together with the excipient.

The pharmaceutical compositions of the invention may be administered to any patient which may experience the beneficial effects of the mixed disulfide conjugates of thienopyridine compounds of the invention. Foremost among such patients are mammals, e.g., humans, although the invention is not intended to be so limited. Other patients include veterinary animals (cows, sheep, pigs, horses, dogs, cats and the like).

The compounds and pharmaceutical compositions thereof may be administered by any means that achieve their intended purpose. For example, administration may be by parenteral, subcutaneous, intravenous, intramuscular, intraperitoneal, transdermal, buccal, intrathecal, intracranial, intranasal or topical routes. Alternatively, or concurrently, administration may be by the oral route. The dosage administered will be dependent upon the age, health, and weight of the recipient, kind of concurrent treatment, if any, frequency of treatment, and the nature of the effect desired.

The pharmaceutical preparations of the present invention are manufactured in a manner which is itself known, for example, by means of conventional mixing, granulating, dragee-making, dissolving, or lyophilizing processes. Thus, pharmaceutical preparations for oral use can be obtained by combining the active compounds with solid excipients, optionally grinding the resulting mixture and processing the mixture of granules, after adding suitable auxiliaries, if desired or necessary, to obtain tablets or dragee cores.

Suitable excipients are, in particular, fillers such as saccharides, for example lactose or sucrose, mannitol or sorbitol, cellulose preparations and/or calcium phosphates, for example tricalcium phosphate or calcium hydrogen phosphate, as well as binders such as starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents may be added such as the above-mentioned starches and also carboxymethyl-starch, cross-linked polyvinyl pyrrolidone, agar, or alginic acid or a salt thereof, such as sodium alginate. Auxiliaries are, above all, flow-regulating agents and lubricants, for example, silica, talc, stearic acid or salts thereof, such as magnesium stearate or calcium stearate, and/or polyethylene glycol. Dragee cores are provided with suitable coatings which, if desired, are resistant to gastric juices. For this purpose, concentrated saccharide solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropylmethyl-cellulose phthalate, are used. Dye stuffs or pigments may be added to the tablets or dragee coatings, for example, for identification or in order to characterize combinations of active compound doses.

Other pharmaceutical preparations which can be used orally include push-fit capsules made of gelatin, as well as soft, sealed capsules made of gelatin and a plasticizer such as glycerol or sorbitol. The push-fit capsules can contain the active compounds in the form of granules which may be mixed with fillers such as lactose, binders such as starches, and/or lubricants such as talc or magnesium stearate and, optionally, stabilizers. In soft capsules, the active compounds are in one embodiment dissolved or suspended in suitable liquids, such as fatty oils, or liquid paraffin. In addition, stabilizers may be added.

Possible pharmaceutical preparations which can be used rectally include, for example, suppositories, which consist of a combination of one or more of the active compounds with a suppository base. Suitable suppository bases are, for example, natural or synthetic triglycerides, or paraffin hydrocarbons. In addition, it is also possible to use gelatin rectal capsules which consist of a combination of the active compounds with a base. Possible base materials include, for example, liquid triglycerides, polyethylene glycols, or paraffin hydrocarbons.

Suitable formulations for parenteral administration include aqueous solutions of the active compounds in water-soluble form, for example, water-soluble salts and alkaline solutions. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides or polyethylene glycol-400. Aqueous injection suspensions may contain substances which increase the viscosity of the suspension include, for example, sodium carboxymethyl cellulose, sorbitol, and/or dextran. Optionally, the suspension may also contain stabilizers.

The topical compositions of this invention are formulated in one embodiment as oils, creams, lotions, ointments and the like by choice of appropriate carriers. Suitable carriers include vegetable or mineral oils, white petrolatum (white soft paraffin), branched chain fats or oils, animal fats and high molecular weight alcohol (greater than C12). The carriers may be those in which the active ingredient is soluble. Emulsifiers, stabilizers, humectants and antioxidants may also be included as well as agents imparting color or fragrance, if desired.

Additionally, transdermal penetration enhancers can be employed in these topical formulations. Examples of such enhancers can be found in U.S. Pat. Nos. 3,989,816 and 4,444,762.

Ointments may be formulated by mixing a solution of the active ingredient in a vegetable oil such as almond oil with warm soft paraffin and allowing the mixture to cool. A typical example of such an ointment is one which includes about 30% almond oil and about 70% white soft paraffin by weight. Lotions may be conveniently prepared by dissolving the active ingredient, in a suitable high molecular weight alcohol such as propylene glycol or polyethylene glycol.

One of ordinary skill in the art will readily recognize that the foregoing represents merely a detailed description of certain preferred embodiments of the present invention. Various modifications and alterations of the compositions and methods described above can readily be achieved using expertise available in the art and are within the scope of the invention.

EXPERIMENTAL

Example I

This example describes stereo-selective synthesis of heterocyclic conjugates of thienopyridine compounds.

The following synthetic reaction scheme:

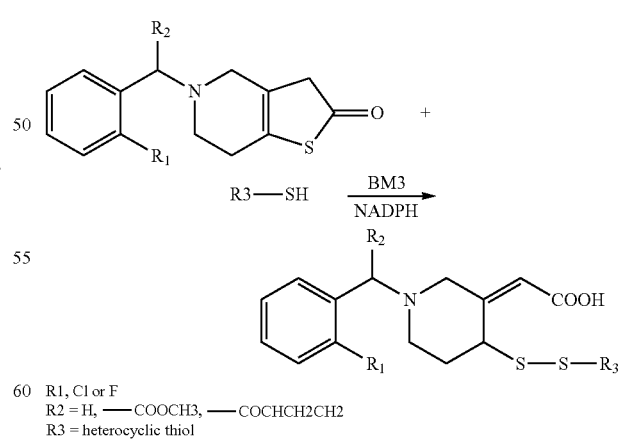

R1, Cl or F
R2 = H, —COOCH3, —COCHCH2CH2
R3 = heterocyclic thiol proceeded by mixing reactants 2-oxo thienopyridine and heterocyclic thiols in the presence of reducing reagent NADPH or NADH and BM3 as catalyst. The reaction did not require any special reactors and apparatus, nor did it require high temperature and pressure usually needed for chemical synthesis. The reaction went completion at ambient temperature in less than 60 min. A range of heterocyclic thiols were tested including, but not limited to, the following shown in Table 1.

TABLE 1

| Chemical Name | Abbreviation |
|---|---|
| 3-nitropyridine-2-thiol | NPT |
| 2-mercaptopyridine | MP |
| 2-mercapto-6-methylpyridine | MMP |
| 5-chloropyridine-2-thiol | 5-CPT |
| 2-mercapto-5-trifluoromethyl-pyridine | 5-TMP |
| 3-(trifluoromethyl)pyridine-2-thiol | 3-TMP |
| 2-mercaptopyridine-3-carbonitrile | MPC |
| 4,6-dimethyl-2-thioxo-1,2-dihydropyridine-3-carbonitrile | DTDC |
| 2-quinolinethiol | QT |
| 1-amino-3-mercaptoisoquinoline | AMP |
| 6-chloropyridazine-3-thiol | CPT |
| 2,5-dimethylfuran-3-thiol | DFT |

FIG. 1 shows the results of HPLC analysis for formation of mixed disulfide conjugate of clopidogrel with five representative compounds. The latter "S" stands for the elution peak of reactant (±)-2-oxo-clopidogrel while the asterisk stands for observed stereoisomer products with respective thiols. As expected, only 2-oxoclopidogrel was detected at 254 nm in the control sample where NADPH is absent. In the presence of NADPH, product peaks marked by asterisks are observed, indicative of product formation as illustrated in the above synthetic reaction scheme. It has been previously reported that metabolism of (±)-2-oxo-clopidogrel in the presence of non-cyclic thiols produces two pairs of product peaks including both trans and cis pairs (see, e.g., Zhang, H., Lauver, D. A., and Hollenberg, P. F. (2014) Thromb. Haemost. 112, 1304-1311). As shown in the above synthetic reaction scheme, four stereoisomers were observed at 350 nm, where 2-oxo-clopidogrel does not absorb, in the presence of glutathione (GSH). Two of the four stereoisomers co-eluted with 2-oxo-clopidogrel. In the test set of heterocyclic thiols only a single or a pair of product peaks was observed, indicating that reaction is stereo-selective for cis products as previously demonstrated (see, e.g., Zhang, H., Lauver, D. A., and Hollenberg, P. F. (2014) Thromb. Haemost. 112, 1304-1311). Structural analysis by X-ray crystallography also confirmed the cis conformation. The stereo-selectivity was also demonstrated in the case of 3-TMT and 5-TMP. The two heterocyclic thiols were identical except for the position of -CF3 group. However in the presence of 3-TMT the amount of product was over ten-fold more than that in the presence of 5-TMP.

Figure 2:
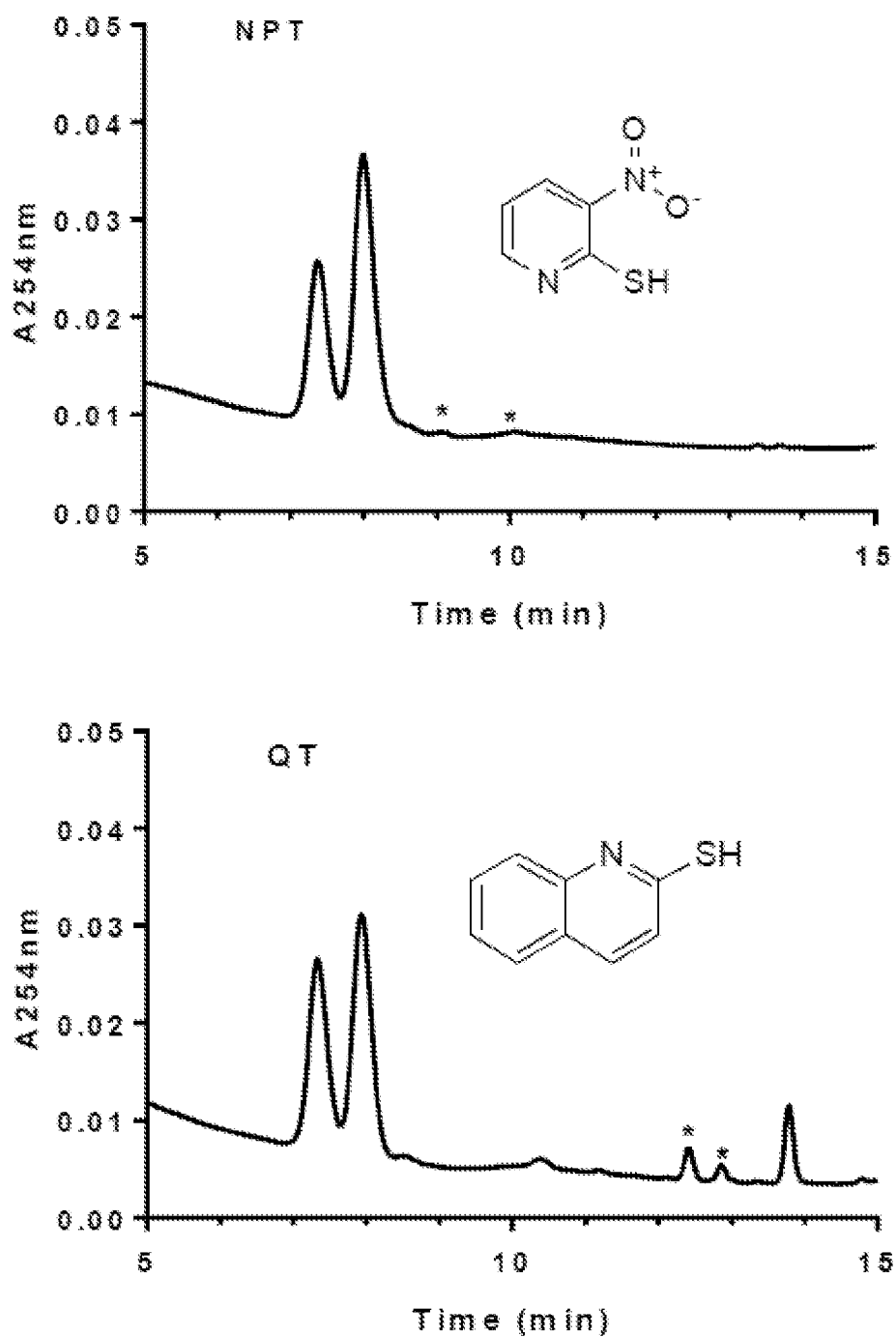
FIG. 2: HPLC analyses of products of mixed disulfide conjugate of clopidogrel. The reaction was performed by mixing (±)-2-oxoclopidogrel, heterocyclic thiol, rat LM, and NADPH at 25° C. for 20 min.

FIG. 2 shows HPLC analyses of products of mixed disulfide conjugate of clopidogrel. The reaction was performed by mixing (±)-2-oxoclopidogrel, heterocyclic thiol, rat LM, and NADPH at 25° C. for 20 min.

Figure 3:
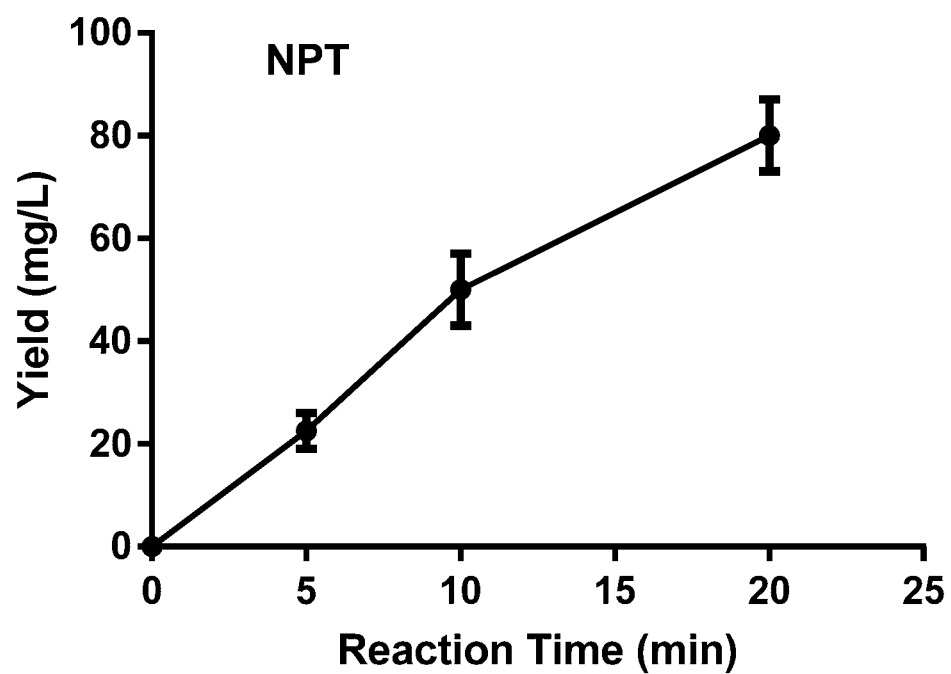
FIG. 3: Yield for synthesis of ClopNPT in the presence of BM3. The reaction was carried out at 25° C.

In comparison, the yields of synthesis in rat liver microsomes (LM) are significantly less than in BM3 for all the test compounds listed in Table 1. For example, in the case of NPT and QT, the amount of the product is over ten-fold less in rat LM compared with in BM3 as shown in FIG. 1. It is clear that synthesis in BM3 is superior to rat LM with respect to yield and stereo-selectivity. Quantitative analysis shows that ~80 mg NPT conjugate can be produced from one liter of reaction mixture as shown in FIG. 3.

Example II

This example describes the genetic engineering of BM3 variants to enhance the productivity of synthesizing mixed disulfide conjugates of thienopyridine compounds.

Improving Over-Expression of BM3 in Bacterial Cells

Experiments were conducted that optimized gene expression of BM3 by re-designing the cDNA of BM3. The re-designed cDNA optimize codon usage for over-expression in bacteria and eliminated structural barriers for transcription. The optimized cDNA for genetically engineered variant of cytochrome P450 BM3 or CYP102A1 is shown in FIG. 4 and encodes 1054 amino acid residues including a hexaHis tag at N-terminus for affinity purification if needed.

Over-Xxpression of BM3 in Bacterial Cells

After cloning the cDNA of BM3 to various vectors such as pCWori, pET28, and pLW01, experiments were conducted that over-expressed BM3 from the constructed plasmid in various bacterial cells including BL21(DE3), C41 (DE3), Topp3, and DH5α. The plasmids were transformed to these cells and expressed in Terric Broth media in the presence of ampicillin for 16 hours at 30° C. after induction by 0.6 mM isopropyl β-D-1-thiogalactopyranoside. A high level of expression was achieved at 0.5-1 g BM3 protein per liter of cell culture. For synthesis of the conjugates only cytosolic fraction of bacterial cells was required and there was no need to purify BM3 by chromatography.

BM3 Mutants with Enhanced Activity for Synthesis of Mixed Disulfide Conjugates of Thienopyridines with Heterocyclic Thiols The natural substrate of BM3 is long chain fatty acid and thus it shows little activity for small molecule drugs. Thus BM3 was engineered by site-directed mutagenesis and direct evolution to select BM3 variants for synthesis of mixed disulfide conjugates of thienopyridines compounds.

After screening a library of BM3 mutants, experiments were conducted that identified "s" number of BM3 variants exhibiting activity for synthesis of mixed disulfide conjugate of thienopyridines compounds. These mutants are listed in Table 2 (variants of wild type amino acid sequence shown in FIG. 4B). The activity was normalized to that of Variant M1. Seven of these variants show activity for synthesis of mixed disulfide conjugate of thienopyridines compounds as shown in Table 3.

TABLE 2

BM3 mutants possessing activity for producing mixed disulfide conjugate of thienopyrdine compounds. The mutants were enerated by either random mutagenesis or rational design.

| BM3 Mutants | Mutations |
|---|---|
| M1 | A82F |
| M2 | A82F/L188Q |
| M3 | A82F/L188Q/R47L |
| M4 | A82F/L188Q/R47L/F87V |
| M5 | A82F/F87V |
| M6 | A82F/F87V/R47L |
| M7 | A82F/F87V/L188Q |
| M8 | A82F/R47L |
| M9 | R47L/F87V/L188Q |

TABLE 2-continued

BM3 mutants possessing activity for producing mixed
disulfide conjugate of thienopyrdine compounds. The mutants were
enerated by either random mutagenesis or rational design.

| BM3 Mutants | Mutations |
|---|---|
| M18 | A82F/T365N |
| M27 | A82F/F87V/L188Q/H116Q |
| M29 | A82F/F87V/L188Q/K31T |
| M31 | A82F/F87V/L188Q/S56R/A135S |
| M32 | A82F/F87V/L188Q/V299D/I458F/P481H |
| M34 | A82F/W1046A |
| M35 | A82F/L188Q/R47L/F87V/W1046A |
| M36 | A82F/F87V/L188Q/W1046A |
| M37 | A82F/F87V/L188Q/W1046L |
| M40 | A82F/F87V/L188Q/K31T/W1046A |

TABLE 3

Reactions were performed in the presence of 0.25 μM BM3.

| Variant | Yield (mg/L) |
|---|---|
| M1 | 18 |
| M4 | 9.2 |
| M7 | 33.1 |
| M9 | 21.4 |
| M13 | 14.1 |
| M16 | 8.8 |
| M37 | 16.7 |

Example III

This example describes the construction, over-expression, and purification of various forms of CYP102A1.

The cDNA sequence encoding a full-length CYP102A1 A82F mutant gene was synthesized by Blue Heron Biotechnology (Bothell, WA). The coding region was then cloned to a pCWori vector using a pair of NdeI/NotI restriction sites. To facilitate purification, a hexa-His tag (6xHistag) sequence was introduced to the N-terminus after the start codon ATG to construct the plasmid of pCW-CYP102A1A82F6xHis. Truncated and FLAG-tagged CYP102A1 were constructed by polymerase chain reaction (PCR) using pCW-CYP102A1A82F6xHis as template DNA and a pair of primers.

All forms of CYP102A1 constructs were over-expressed in C41(DE3) cells in the presence of 0.1 mg/mL ampicillin. In brief, a single colony from the C41(DE3) cells transformed with the pCWori plasmid containing the desired gene was inoculated to 50 mL Luria-Bertani (LB) medium and the culture was grown at 30° C./180 rpm overnight. An aliquot of 10 mL of the LB culture was used to inoculate 1 L Terric Broth (TB) medium. The TB medium was grown for 6 hr and over-expression of CYP102A1 was induced by the addition of 0.6 mM Isopropyl β-D-1-thiogalactopyranoside (IPTG) and 0.5 mM δ-aminolevulinic acid. The induced cells were continued to grow for 16 hr at 30° C. and then harvested by centrifugation at 2,500 g for 25 min. All proteins were purified with a Histrap HP column (5 mL, GE Health Sciences) as reported previously (see, e.g., Zhang, H., et al., (2013) Biochemistry 52, 355-364). The purified proteins were desalted to 0.1 M KPi/15% glycerol buffer (pH 7.4) using PD-10 columns (GE Health Sciences) and stored in aliquots at −80° C. until use.

Having now fully described the invention, it will be understood by those of skill in the art that the same can be performed within a wide and equivalent range of conditions, formulations, and other parameters without affecting the scope of the invention or any embodiment thereof. All patents, patent applications and publications cited herein are fully incorporated by reference herein in their entirety.

INCORPORATION BY REFERENCE

The entire disclosure of each of the patent documents and scientific articles referred to herein is incorporated by reference for all purposes.

EQUIVALENTS

The invention may be embodied in other specific forms without departing from the spirit or essential characteristics thereof. The foregoing embodiments are therefore to be considered in all respects illustrative rather than limiting the invention described herein. Scope of the invention is thus indicated by the appended claims rather than by the foregoing description, and all changes that come within the meaning and range of equivalency of the claims are intended to be embraced therein.

What is claimed is:

1. A mutant CYP102A1 enzyme capable of catalyzing conjugation between 2-oxo thienopyridine and heterocyclic thiols in the presence of a reducing reagent, wherein the reducing agent is NADPH or NADH,
   wherein the mutant CYP102A1 enzyme comprises SEQ ID NO: 2 and having substitutions selected from: A82F/L188Q, A82F/L188Q/R47L, A82F/F87V/R47L, A82F/F87V/L188Q, A82F/R47L, A82F/T365N, A82F/F87V/L188Q/H116Q, A82F/F87V/L188Q/K31T, A82F/F87V/L188Q/S56R/A135S, A82F/F87V/L188Q/V299D/I458F/P481H, A82F/W1046A, A82F/L188Q/R47L/F87V/W1046A, A82F/F87V/L188Q/W1046A, A82F/F87V/L188Q/W1046L, and A82F/F87V/L188Q/K31T/W1046A.

2. The mutant CYP102A1 enzyme of claim 1, wherein the catalyzing of conjugation between 2-oxo thienopyridine and heterocyclic thiols in the presence of a reducing reagent results in the generation of mixed disulfide conjugates of thienopyridine compounds.

3. The mutant CYP102A1 enzyme of claim 1, wherein the catalyzing of conjugation between 2-oxo thienopyridine and heterocyclic thiols in the presence of a reducing reagent selectively generates cis stereoisomers of the mixed disulfide conjugates of thienopyridine compounds.

4. The mutant CYP102A1 enzyme of claim 1, wherein the enzyme is encoded by a nucleic acid sequence having at least 99% homology with SEQ ID NO: 1.

5. The mutant CYP102A1 enzyme of claim 1, wherein the enzyme is encoded by a nucleic acid sequence having at least 100% homology with SEQ ID NO: 3.

6. A method for synthesizing cis stereoisomers of mixed disulfide conjugates of thienopyridine compounds, comprising mixing a 2-oxo thienopyridine moiety, a heterocyclic thiol moiety, and the mutant CYP102A1 enzyme of claim 1 in the presence of a reducing reagent, wherein the reducing agent is NADPH or NADH.

7. The method of claim 6, wherein the 2-oxo thienopyridine moiety is represented by

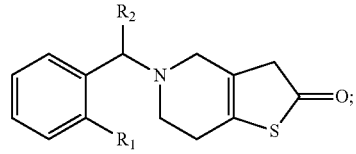

wherein R1 is either Chlorine or Fluorine; wherein R2 is H, COOCH3, or COCHCH2CH2.

8. The method of claim 6, wherein the heterocyclic thiol moiety is represented by R3-SH; wherein R3 is selected from 3-nitropyridine-2-thiol, 2-mercaptopyridine, 2-mercapto-6-methylpyridine, 5-chloropyridine-2-thiol, 2-mercapto-5-trifluoromethyl-pyridine, 3-(trifluoromethyl) pyridine-2-thiol, 2-mercaptopyridine-3-carbonitrile, 4,6-dimethyl-2-thioxo-1,2-dihydropyridine-3-carbonitrile, 2-quinolinethiol, 1-amino-3-mercaptoisoquinoline, 6-chloropyridazine-3-thiol, and 2,5-dimethylfuran-3-thiol.

9. The method of claim 6, wherein the mixing occurs at ambient temperature, wherein the mixing occurs for a time period between twenty and sixty minutes.

10. The method of claim 6, wherein the mutant CYP102A1 enzyme is comprised within a bacterial cytosolic fraction.

11. The method of claim 6, wherein the amount of mutant CYP102A1 enzyme is between approximately 0.1 and 1 μM.

12. The method of claim 6, wherein the mixing results in the generation of approximately 100 mg of cis stereoisomers of mixed disulfide conjugates of thienopyridine compounds per liter of the 2-oxo thienopyridine moiety, the heterocyclic thiol moiety, the mutant CYP102A1 enzyme, and the reducing agent.

13. A method of treating, ameliorating, or preventing a cardiovascular disease in a patient comprising administering to said patient a therapeutically effective amount of a compound generated with the method of claim 6.

14. The method of claim 13, wherein said administration is selected from the group consisting of oral administration and intravenous administration.

15. The method of claim 13, wherein said cardiovascular disease is selected from the group consisting of coronary artery disease, peripheral vascular disease, atherothrombosis, and cerebrovascular disease.

16. The method of claim 13, wherein said compound reduces aggregation of platelets.

17. The method of claim 16, wherein said reduces aggregation of said platelets occurs through
   irreversible binding to $P2Y_{12}$ receptors and/or blocking ADP receptors.

18. The method of claim 13, further comprising co-administration of at least one agent selected from the group consisting of a HMG-CoA reductase inhibitor, an ACE Inhibitor, a Calcium Channel Blocker, a Platelet Aggregation Inhibitor, a Polyunsaturated Fatty Acid, Fibric Acid Derivative, a Bile Acid Sequestrant, an Antioxidant, a Thrombolytic Agent, and an Antianginal Agent.

* * * * *

SEQUENCE LISTING

<160> NUMBER OF SEQ ID NOS: 3

<210> SEQ ID NO 1
<211> LENGTH: 3150
<212> TYPE: DNA
<213> ORGANISM: artificial sequence
<220> FEATURE:
<223> OTHER INFORMATION: synthetic

<400> SEQUENCE: 1

```
atgacaatta aagaaatgcc tcagccaaaa acgtttggag agcttaaaaa tttaccgtta      60
ttaaacacag ataaaccggt tcaagctttg atgaaaattg cggatgaatt aggagaaatc     120
tttaaattcg aggcgcctgg tcgtgtaacg cgctacttat caagtcagcg tctaattaaa     180
gaagcatgcg atgaatcacg ctttgataaa aacttaagtc aagcgcttaa atttgtacgt     240
gattttgcag gagacgggtt atttacaagc tggacgcatg aaaaaaattg gaaaaaagcg     300
cataatatct tacttccaag cttcagtcag caggcaatga aggctatca tgcgatgatg     360
```

```
gtcgatatcg ccgtgcagct tgttcaaaag tgggagcgtc taaatgcaga tgagcatatt    420
gaagtaccgg aagacatgac acgtttaacg cttgatacaa ttggtctttg cggctttaac    480
tatcgcttta acagctttta ccgagatcag cctcatccat ttattacaag tatggtccgt    540
gcactggatg aagcaatgaa caagctgcag cgagcaaatc cagacgaccc agcttatgat    600
gaaaacaagc gccagtttca agaagatatc aaggtgatga acgacctagt agataaaatt    660
attgcagatc gcaaagcaag cggtgaacaa agcgatgatt tattaacgca tatgctaaac    720
ggaaaagatc cagaaacggg tgagccgctt gatgacgaga acattcgcta tcaaattatt    780
acattcttaa ttgcgggaca cgaaacaaca agtggtcttt tatcatttgc gctgtatttc    840
ttagtgaaaa atccacatgt attacaaaaa gcagcagaag aagcagcacg agttctagta    900
gatcctgttc caagctacaa acaagtcaaa cagcttaaat atgtcggcat ggtcttaaac    960
gaagcgctgc gcttatggcc aactgctcct gcgttttccc tatatgcaaa agaagatacg   1020
gtgcttggag gagaatatcc tttagaaaaa ggcgacgaac taatggttct gattcctcag   1080
cttcaccgtg ataaaacaat tggggagac gatgtggaag agttccgtcc agagcgtttt   1140
gaaaatccaa gtgcgattcc gcagcatgcg tttaaaccgt ttggaaacgg tcagcgtgcg   1200
tgtatcggtc agcagttcgc tcttcatgaa gcaacgctgg tacttggtat gatgctaaaa   1260
cactttgact ttgaagatca tacaaactac gagctggata ttaaagaaac tttaacgtta   1320
aaacctgaag gctttgtggt aaaagcaaaa tcgaaaaaaa ttccgcttgg cggtattcct   1380
tcacctagca ctgaacagtc tgctaaaaaa gtacgcaaaa aggcagaaaa cgctcataat   1440
acgccgctgc ttgtgctata cggttcaaat atgggaacag ctgaaggaac ggcgcgtgat   1500
ttagcagata ttgcaatgag caaaggattt gcaccgcagg tcgcaacgct tgattcacac   1560
gccggaaatc ttccgcgcga aggagctgta ttaattgtaa cggcgtctta taacggtcat   1620
ccgcctgata acgcaaagca atttgtcgac tggttagacc aagcgtctgc tgatgaagta   1680
aaaggcgttc gctactccgt atttggatgc ggcgataaaa actgggctac tacgtatcaa   1740
aaagtgcctg ctttatcga tgaaacgctt gccgctaaag gggcagaaaa catcgctgac   1800
cgcggtgaag cagatgcaag cgacgacttt gaaggcacat atgaagaatg gcgtgaacat   1860
atgtggagtg acgtagcagc ctactttaac ctcgacattg aaaacagtga agataataaa   1920
tctactcttt cacttcaatt tgtcgacagc gccgcggata tgccgcttgc gaaaatgcac   1980
ggtgcgtttt caacgaacgt cgtagcaagc aaagaacttc aacagccagg cagtgcacga   2040
agcacgcgac atcttgaaat tgaacttcca aaagaagctt cttatcaaga aggagatcat   2100
ttaggtgtta ttcctcgcaa ctatgaagga atagtaaacc gtgtaacagc aaggttcggc   2160
ctagatgcat cacagcaaat ccgtctgaa gcagaagaag aaaaattagc tcatttgcca   2220
ctcgctaaaa cagtatccgt agaagagctt ctgcaatacg tggagcttca agatcctgtt   2280
acgcgcacgc agcttcgcgc aatggctgct aaaacggtct gcccgccgca taaagtagag   2340
cttgaagcct tgcttgaaaa gcaagcctac aaagaacaag tgctggcaaa acgtttaaca   2400
atgcttgaac tgcttgaaaa atacccggcg tgtgaaatga aattcagcga atttatcgcc   2460
cttctgccaa gcatacgccc gcgctattac tcgatttctt catcacctcg tgtcgatgaa   2520
aaacaagcaa gcatcacggt cagcgttgtc tcaggagaag cgtggagcgg atatggagaa   2580
tataaaggaa ttgcgtcgaa ctatcttgcc gagctgcaag aaggagatac gattacgtgc   2640
tttatttcca caccgcagtc agaatttacg ctgccaaaag accctgaaac gccgcttatc   2700
```

-continued

```
atggtcggac cgggaacagg cgtcgcgccg tttagaggct ttgtgcaggc gcgcaaacag  2760
ctaaaagaac aaggacagtc acttggagaa gcacatttat acttcggctg ccgttcacct  2820
catgaagact atctgtatca agaagagctt gaaaacgccc aaagcgaagg catcattacg  2880
cttcataccg cttttctcg catgccaaat cagccgaaaa catacgttca gcacgtaatg  2940
gaacaagacg gcaagaaatt gattgaactt cttgatcaag gagcgcactt ctatatttgc  3000
ggagacggaa gccaaatggc acctgccgtt gaagcaacgc ttatgaaaag ctatgctgac  3060
gttcaccaag tgagtgaagc agacgctcgc ttatggctgc agcagctaga agaaaaggc  3120 cgatacgcaa aagacgtgtg ggctgggtaa                                    3150
```

<210> SEQ ID NO 2
<211> LENGTH: 1048
<212> TYPE: PRT
<213> ORGANISM: artificial sequence
<220> FEATURE:
<223> OTHER INFORMATION: synthetic

<400> SEQUENCE: 2

```
Thr Ile Lys Glu Met Pro Gln Pro Lys Thr Phe Gly Glu Leu Lys Asn
1               5                   10                  15

Leu Pro Leu Leu Asn Thr Asp Lys Pro Val Gln Ala Leu Met Lys Ile
            20                  25                  30

Ala Asp Glu Leu Gly Glu Ile Phe Lys Phe Glu Ala Pro Gly Arg Val
        35                  40                  45

Thr Arg Tyr Leu Ser Ser Gln Arg Leu Ile Lys Glu Ala Cys Asp Glu
    50                  55                  60

Ser Arg Phe Asp Lys Asn Leu Ser Gln Ala Leu Lys Phe Val Arg Asp
65                  70                  75                  80

Phe Ala Gly Asp Gly Leu Phe Thr Ser Trp Thr His Glu Lys Asn Trp
                85                  90                  95

Lys Lys Ala His Asn Ile Leu Leu Pro Ser Phe Ser Gln Gln Ala Met
            100                 105                 110

Lys Gly Tyr His Ala Met Met Val Asp Ile Ala Val Gln Leu Val Gln
        115                 120                 125

Lys Trp Glu Arg Leu Asn Ala Asp Glu His Ile Glu Val Pro Glu Asp
    130                 135                 140

Met Thr Arg Leu Thr Leu Asp Thr Ile Gly Leu Cys Gly Phe Asn Tyr
145                 150                 155                 160

Arg Phe Asn Ser Phe Tyr Arg Asp Gln Pro His Pro Phe Ile Thr Ser
                165                 170                 175

Met Val Arg Ala Leu Asp Glu Ala Met Asn Lys Leu Gln Arg Ala Asn
            180                 185                 190

Pro Asp Asp Pro Ala Tyr Asp Glu Asn Lys Arg Gln Phe Gln Glu Asp
        195                 200                 205

Ile Lys Val Met Asn Asp Leu Val Asp Lys Ile Ala Asp Arg Lys
    210                 215                 220

Ala Ser Gly Glu Gln Ser Asp Asp Leu Leu Thr His Met Leu Asn Gly
225                 230                 235                 240

Lys Asp Pro Glu Thr Gly Glu Pro Leu Asp Asp Glu Asn Ile Arg Tyr
                245                 250                 255

Gln Ile Ile Thr Phe Leu Ile Ala Gly His Glu Thr Thr Ser Gly Leu
            260                 265                 270

Leu Ser Phe Ala Leu Tyr Phe Leu Val Lys Asn Pro His Val Leu Gln
        275                 280                 285
```

```
Lys Ala Ala Glu Glu Ala Ala Arg Val Leu Val Asp Pro Val Pro Ser
    290                 295                 300
Tyr Lys Gln Val Lys Gln Leu Lys Tyr Val Gly Met Val Leu Asn Glu
305                 310                 315                 320
Ala Leu Arg Leu Trp Pro Thr Ala Pro Ala Phe Ser Leu Tyr Ala Lys
                325                 330                 335
Glu Asp Thr Val Leu Gly Gly Glu Tyr Pro Leu Glu Lys Gly Asp Glu
            340                 345                 350
Leu Met Val Leu Ile Pro Gln Leu His Arg Asp Lys Thr Ile Trp Gly
        355                 360                 365
Asp Asp Val Glu Glu Phe Arg Pro Glu Arg Phe Glu Asn Pro Ser Ala
    370                 375                 380
Ile Pro Gln His Ala Phe Lys Pro Phe Gly Asn Gly Gln Arg Ala Cys
385                 390                 395                 400
Ile Gly Gln Gln Phe Ala Leu His Glu Ala Thr Leu Val Leu Gly Met
                405                 410                 415
Met Leu Lys His Phe Asp Phe Glu Asp His Thr Asn Tyr Glu Leu Asp
            420                 425                 430
Ile Lys Glu Thr Leu Thr Leu Lys Pro Glu Gly Phe Val Val Lys Ala
        435                 440                 445
Lys Ser Lys Lys Ile Pro Leu Gly Gly Ile Pro Ser Pro Ser Thr Glu
    450                 455                 460
Gln Ser Ala Lys Lys Val Arg Lys Lys Ala Glu Asn Ala His Asn Thr
465                 470                 475                 480
Pro Leu Leu Val Leu Tyr Gly Ser Asn Met Gly Thr Ala Glu Gly Thr
                485                 490                 495
Ala Arg Asp Leu Ala Asp Ile Ala Met Ser Lys Gly Phe Ala Pro Gln
            500                 505                 510
Val Ala Thr Leu Asp Ser His Ala Gly Asn Leu Pro Arg Glu Gly Ala
        515                 520                 525
Val Leu Ile Val Thr Ala Ser Tyr Asn Gly His Pro Pro Asp Asn Ala
    530                 535                 540
Lys Gln Phe Val Asp Trp Leu Asp Gln Ala Ser Ala Asp Glu Val Lys
545                 550                 555                 560
Gly Val Arg Tyr Ser Val Phe Gly Cys Gly Asp Lys Asn Trp Ala Thr
                565                 570                 575
Thr Tyr Gln Lys Val Pro Ala Phe Ile Asp Glu Thr Leu Ala Ala Lys
            580                 585                 590
Gly Ala Glu Asn Ile Ala Asp Arg Gly Glu Ala Asp Ala Ser Asp Asp
        595                 600                 605
Phe Glu Gly Thr Tyr Glu Glu Trp Arg Glu His Met Trp Ser Asp Val
    610                 615                 620
Ala Ala Tyr Phe Asn Leu Asp Ile Glu Asn Ser Glu Asp Asn Lys Ser
625                 630                 635                 640
Thr Leu Ser Leu Gln Phe Val Asp Ser Ala Ala Asp Met Pro Leu Ala
                645                 650                 655
Lys Met His Gly Ala Phe Ser Thr Asn Val Val Ala Ser Lys Glu Leu
            660                 665                 670
Gln Gln Pro Gly Ser Ala Arg Ser Thr Arg His Leu Glu Ile Glu Leu
        675                 680                 685
Pro Lys Glu Ala Ser Tyr Gln Glu Gly Asp His Leu Gly Val Ile Pro
    690                 695                 700
```

Arg Asn Tyr Glu Gly Ile Val Asn Arg Val Thr Ala Arg Phe Gly Leu
705                 710                 715                 720

Asp Ala Ser Gln Gln Ile Arg Leu Glu Ala Glu Glu Lys Leu Ala
            725                 730                 735

His Leu Pro Leu Ala Lys Thr Val Ser Val Glu Glu Leu Leu Gln Tyr
            740                 745                 750

Val Glu Leu Gln Asp Pro Val Thr Arg Thr Gln Leu Arg Ala Met Ala
            755                 760                 765

Ala Lys Thr Val Cys Pro Pro His Lys Val Glu Leu Glu Ala Leu Leu
    770                 775                 780

Glu Lys Gln Ala Tyr Lys Glu Gln Val Leu Ala Lys Arg Leu Thr Met
785                 790                 795                 800

Leu Glu Leu Leu Glu Lys Tyr Pro Ala Cys Glu Met Lys Phe Ser Glu
                805                 810                 815

Phe Ile Ala Leu Leu Pro Ser Ile Arg Pro Arg Tyr Tyr Ser Ile Ser
            820                 825                 830

Ser Ser Pro Arg Val Asp Glu Lys Gln Ala Ser Ile Thr Val Ser Val
            835                 840                 845

Val Ser Gly Glu Ala Trp Ser Gly Tyr Gly Glu Tyr Lys Gly Ile Ala
850                 855                 860

Ser Asn Tyr Leu Ala Glu Leu Gln Glu Gly Asp Thr Ile Thr Cys Phe
865                 870                 875                 880

Ile Ser Thr Pro Gln Ser Glu Phe Thr Leu Pro Lys Asp Pro Glu Thr
                885                 890                 895

Pro Leu Ile Met Val Gly Pro Gly Thr Gly Val Ala Pro Phe Arg Gly
            900                 905                 910

Phe Val Gln Ala Arg Lys Gln Leu Lys Glu Gln Gly Gln Ser Leu Gly
            915                 920                 925

Glu Ala His Leu Tyr Phe Gly Cys Arg Ser Pro His Glu Asp Tyr Leu
930                 935                 940

Tyr Gln Glu Glu Leu Glu Asn Ala Gln Ser Glu Gly Ile Ile Thr Leu
945                 950                 955                 960

His Thr Ala Phe Ser Arg Met Pro Asn Gln Pro Lys Thr Tyr Val Gln
                965                 970                 975

His Val Met Glu Gln Asp Gly Lys Lys Leu Ile Glu Leu Leu Asp Gln
            980                 985                 990

Gly Ala His Phe Tyr Ile Cys Gly Asp Gly Ser Gln Met Ala Pro Ala
            995                 1000                1005

Val Glu Ala Thr Leu Met Lys Ser Tyr Ala Asp Val His Gln Val
    1010                1015                1020

Ser Glu Ala Asp Ala Arg Leu Trp Leu Gln Gln Leu Glu Glu Lys
    1025                1030                1035

Gly Arg Tyr Ala Lys Asp Val Trp Ala Gly
    1040                1045

<210> SEQ ID NO 3
<211> LENGTH: 3162
<212> TYPE: DNA
<213> ORGANISM: artificial sequence
<220> FEATURE:
<223> OTHER INFORMATION: synthetic

<400> SEQUENCE: 3
atgcaccatc atcatcatca tattaaggag atgccgcagc caaaaacatt cggcgaactc     60
aaaaacttac cattactgaa taccgacaaa ccggtccaag cactgatgaa aattgcggac    120

| | |
|---|---|
| gaattaggtg aaatcttcaa attcgaggcg cccggtcgcg taacacgtta tttatccagt | 180 |
| cagcgcctta tcaaagaagc gtgtgatgaa agtcgttttg ataaaaatct gtcccaggca | 240 |
| cttaaatttg ttcgtgactt tttcggtgat ggcctgttta cctcttggac tcatgaaaaa | 300 |
| aactggaaaa aagcgcataa tatcttgctt ccgtcgtttt cgcagcaggc aatgaaaggt | 360 |
| taccatgcca tgatggtcga tattgccgtc cagctggtgc aaaaatggga acgtcttaac | 420 |
| gctgatgaac atattgaagt gcccgaagac atgacccgtc tgacgctgga tactattgga | 480 |
| ctgtgcgggt tcaactatcg tttcaactcc ttctaccgtg atcagccaca tccgtttatt | 540 |
| acttctatgg tccgcgcctt agacgaagcc atgaacaaac tgcagcgcgc caacccagac | 600 |
| gacccagctt atgatgagaa taaacgtcag tttcaagaag acatcaaagt catgaacgac | 660 |
| ttagtggata aaattattgc agaccgtaaa gcgagcggcg aacagagtga tgacctgctt | 720 |
| acccacatgc tgaatggtaa agatccagag accggcgagc cgttagatga tgaaaatatt | 780 |
| cgctaccaga tcattacctt tttaatcgca ggacacgaaa caacaagtgg actgctcagc | 840 |
| tttgcactct actttctggt taaaaacccg catgttctgc aaaaagcagc ggaagaggcc | 900 |
| gcccgtgtgc tggtcgatcc ggttccvagc tataaacagg tcaaacagtt aaaatacgtg | 960 |
| ggcatggtct aaacgaggc tctgcgctta tggccaacag caccagcatt ttcgttatat | 1020 |
| gcaaaagaag ataccgttct gggaggagaa taccgttag aaaaaggcga cgagcttatg | 1080 |
| gtgctgatcc cacagttaca ccgtgataaa accatttggg gcgacgatgt ggaagaattt | 1140 |
| cgcccagaac gtttcgagaa ccctagcgca attccacagc atgccttcaa acccttcggg | 1200 |
| aacggtcagc gcgcgtgcat tgggcagcag ttcgcgctgc atgaagcaac tttggtgtta | 1260 |
| ggcatgatgc tgaaacactt tgattttgaa gaccacacga attatgaact ggatattaaa | 1320 |
| gaaaccctga cactgaaacc agaaggattc gtagttaaag cgaaaagcaa aaagattccg | 1380 |
| ctgggtggca ttccgagccc atccaccgaa cagagcgcga aaaagttcg aaaaaggcg | 1440 |
| gaaaatgcgc acaataccccc cttgttagtc ctttacggct caaatatggg cacagcagaa | 1500 |
| ggcaccgcac gtgacttagc cgatattgca atgagcaagg gtttcgcgcc ccaagtcgcg | 1560 |
| accttggatt cacacgctgg aaacctgccg cgggaaggcg ccgtccttat cgttactgcc | 1620 |
| tcatataacg gtcaccctcc ggacaatgcg aaacaatttg tggactggtt agatcaagcc | 1680 |
| tcggccgacg aagtgaaagg cgttcgttat tctgttttg gatgtgggga taaaaactgg | 1740 |
| gcgacgacgt accaaaaagt ccctgctttt attgatgaaa cgttggctgc aaaaggtgca | 1800 |
| gaaaacattg cagaccgtgg cgaagcagac gcgagcgacg actttgaagg tacctatgag | 1860 |
| gaatggcgtg aacacatgtg gagtgatgtc gccgcttact tcaacttaga tattgaaaat | 1920 |
| tccgaagata taaaagtac cctgagcttg caattcgtgg actcggctgc cgacatgccg | 1980 |
| ctcgctaaaa tgcacggggc gtttagtacg aatgtagtgg cttccaaaga gttgcaacaa | 2040 |
| cccggtagcg cacgctcgac ccggcacctg gaaattgaat taccgaagga agcgtcttat | 2100 |
| caggaaggag atcatctggg tgtaatccca cgcaattacg aaggtattgt taatcgcgtt | 2160 |
| accgcgcgtt ttggtttaga tgcctcccaa caaatccgtt tagaagcaga agaagaaaaa | 2220 |
| ctcgcgcatt taccctttagc caaaaccgtt tcggtcgaag aactgctgca atatgttgaa | 2280 |
| cttcaggacc ctgtgacccg tacccagctc cgtgccatgg ccgcgaaaac agtatgccca | 2340 |
| ccccacaaag ttgaattaga ggcgctgtta gagaaacaag catacaaaga acaagtgtta | 2400 |
| gctaagcgtc tgaccatgtt agagttactg gagaaatatc cggcgtgcga gatgaaattc | 2460 |

```
tcagaattca ttgcattgtt gccgagcatt cgtccgcggt attacagtat ctcgagctca    2520
ccgcgcgttg atgaaaaaca ggcctctatt acggtctccg tagtttccgg cgaagcctgg    2580
agcgggtatg gagaatataa aggaattgct agcaactatc tcgcggagct gcaagagggc    2640
gacactatta catgcttcat ttctacgccg caatccgaat ttacactgcc gaaagacccg    2700
gaaacgccac tcattatggt aggcccaggt actggcgtag cgccatttcg cggattcgtt    2760
caggctcgta aacagttgaa agaacaaggt caaagtcttg gcgaagcaca tttatacttc    2820
ggctgccgct cgccgcatga ggactatctc tatcaggaag aattggagaa cgcacagagt    2880
gagggcatta tcaccttgca tacggctttt tctcgcatgc ctaatcaacc taaaacctat    2940
gtccaacatg tgatggagca ggatggaaaa aaattgatcg agctgttgga tcagggcgcg    3000 cattttaca tttgcgggga tggttcgcag atggcacccg ccgtggaggc caccttatg     3060 aaaagctatg cagatgtgca ccaggtaagc gaagcggatg cccgtctgtg gctgcaacag    3120
ttggaagaaa aaggtcgcta tgcaaaagac gtgtgggcag gt                      3162
```